(12) United States Patent
Benoit

(10) Patent No.: US 9,170,265 B2
(45) Date of Patent: Oct. 27, 2015

(54) ELECTRODE, ELECTROCHEMICAL SENSOR AND APPARATUS, AND METHODS FOR OPERATING THE SAME

(75) Inventor: Vincent Benoit, Glasgow (GB)

(73) Assignee: MODE DIAGNOSTICS LIMITED, Glasgow (GB)

( * ) Notice: Subject to any disclaimer, the term of this patent is extended or adjusted under 35 U.S.C. 154(b) by 1205 days.

(21) Appl. No.: 13/128,543

(22) PCT Filed: Nov. 12, 2009

(86) PCT No.: PCT/GB2009/002664
§ 371 (c)(1),
(2), (4) Date: May 10, 2011

(87) PCT Pub. No.: WO2010/055306
PCT Pub. Date: May 20, 2010

(65) Prior Publication Data
US 2011/0213229 A1   Sep. 1, 2011

(30) Foreign Application Priority Data

Nov. 13, 2008   (GB) .................................. 0820817.5

(51) Int. Cl.
*A61B 5/05* (2006.01)
*G01N 33/72* (2006.01)
*G01N 27/327* (2006.01)

(52) U.S. Cl.
CPC .......... *G01N 33/725* (2013.01); *G01N 27/3271* (2013.01); *G01N 33/726* (2013.01)

(58) Field of Classification Search
CPC ............... A61B 5/145; A61B 5/14532; A61B 5/14546; A61B 5/1468; A61B 5/1473; A61B 5/1486
USPC .......................................... 600/345–347, 365
See application file for complete search history.

(56) References Cited

U.S. PATENT DOCUMENTS 3,290,117 A * 12/1966 Haitsma et al. ................ 422/420
4,063,894 A * 12/1977 Ogawa et al. .................... 436/66

(Continued)

FOREIGN PATENT DOCUMENTS

EP          0 233 144 A2      8/1987
JP          A-59-222766      12/1984

(Continued)

OTHER PUBLICATIONS

Broyles et al., "Quantification of Small Amounts of Hemoglobin in Polyacrylamide Gels with Benzidine," *Analytical Biochemistry*, 1979, vol. 94, pp. 211-219.

(Continued)

*Primary Examiner* — Michael D'Angelo
(74) *Attorney, Agent, or Firm* — Oliff PLC

(57) ABSTRACT

A method for amperometric detection of proteins, especially haemoglobin in faeces, using an electrochemical sensor. The electrochemical sensor includes: a working electrode having an electrically conductive matrix holding a first reagent and/or a second reagent, the second reagent being an oxidizing agent, or a precursor thereof, for the first reagent; a counter electrode and optionally a reference electrode; wherein a reaction between the first reagent and the oxidizing agent is catalyzed by the protein to provide a detectable signal at the working electrode. The electrically conductive matrix is an electrically conductive carbon- or graphite-containing matrix or an electrically conductive porous matrix.

33 Claims, 16 Drawing Sheets

(56) References Cited

U.S. PATENT DOCUMENTS

| | | | |
|---|---|---|---|
| 4,225,410 A | | 9/1980 | Pace |
| 4,556,640 A | | 12/1985 | Gantzer |
| 4,587,220 A | | 5/1986 | Mayambala-Mwanika et al. |
| 4,645,743 A | * | 2/1987 | Baker et al. .................... 436/66 |
| 4,876,205 A | | 10/1989 | Green et al. |
| 5,478,754 A | * | 12/1995 | Brandt et al. ................ 436/518 |
| 5,532,138 A | | 7/1996 | Singh et al. |
| 5,695,947 A | | 12/1997 | Guo et al. |
| 5,885,789 A | | 3/1999 | Kardos et al. |
| 6,033,866 A | | 3/2000 | Guo et al. |
| 6,140,045 A | * | 10/2000 | Wohlstadter et al. ........ 435/6.11 |
| 6,175,752 B1 | * | 1/2001 | Say et al. ..................... 600/345 |
| 7,241,627 B2 | * | 7/2007 | Wilhelm et al. ............. 436/518 |
| 2004/0081752 A1 | * | 4/2004 | Lin et al. ....................... 427/123 |
| 2007/0037296 A1 | | 2/2007 | Goulden |
| 2009/0030293 A1 | * | 1/2009 | Cooper et al. ................ 600/302 |
| 2010/0025264 A1 | * | 2/2010 | Yuan et al. ................. 205/777.5 |

FOREIGN PATENT DOCUMENTS

| | | |
|---|---|---|
| JP | A-07-023797 | 1/1995 |
| WO | WO 2005/106498 A1 | 11/2005 |
| WO | WO 2006/085087 A2 | 8/2006 |

OTHER PUBLICATIONS

Caligiore et al., "Peroxidase levels in food: relevance to colorectal cancer screening," *The American Journal of Clinical Nutrition*, 1982, vol. 35, pp. 1487-1489.

Compagnone et al., "Sub-Micromolar Detection of Hydrogen Peroxide at a Peroxidase/Tetramethylbenzidine Solid Carbon Paste Electrode," *Analytical Letters*, vol. 31, No. 7, 1998, pp. 1107-1120.

Conneely et al., "Development of an immunosensor for the detection of testosterone in bovine urine," *Analytica Chimica Acta*, 2007, vol. 583, pp. 153-160.

Data Sheet for Basi Stationary Voltammetry Electrodes from Bioanalytical website, accessed Oct. 22, 2008.

Data Sheet for BQ242 Carbon Conductive Composition from DuPont Microcircuit Materials, accessed Oct. 22, 2008.

Data Sheet for Carbon/Graphite Ink C10903P14 from Gwent Group, Apr. 2008.

Data Sheet for Electrodag PF-407A from Acheson Industries (Europe), Aug. 2009.

Data Sheet for Graphite from Sigma-Aldrich website, accessed Oct. 22, 2008.

Data Sheet for Mineral oil from Sigma-Aldrich website, accessed Oct. 22, 2008.

Data Sheet for Red Blood Cell Lysing Buffer Hybri-Max from Sigma-Aldrich website, accessed Oct. 27, 2008.

Data Sheet for Selector Guide PTF Inks for Flexible Substrates From Acheson Industries (Europe), accessed Oct. 22, 2008.

Del Carlo et al., "Enzyme immunoassay with amperometric flow-injection analysis using horseradish peroxidase as a label. Application to the determination of polychlorinated biphenyls." *Analytica Chimica Acta*, 1996, vol. 336, pp. 167-174.

He et al., "Differential pulse voltammetric enzyme-linked immunoassay for the determination of *Helicobacter pylori* specific immunoglobulin G (IgG) antibody," *Talanta*, 1997, vol. 44, pp. 823-830.

Josephy et al., "The Horseradish Peroxidase-catalyzed Oxidation of 3,5,3',5'-Tetramethylbenzidine," *The Journal of Biological Chemistry*, 1982, vol. 257, No. 7, pp. 3669-3675.

Kurtinaitiene et al., "Amperometric immunosensor for diagnosis of BLV infection," *Biosensors and Bioelectronics*, 2008, vol. 23, pp. 1547-1554.

Liem et al., "Quantitative Determination of Hemoglobin and Cytochemical Staining for Peroxidase Using 3,3',5,5'-Tetramethylbenzidine Dihydrochloride, a Safe Substitute for Benzidine," *Analytical Biochemistry*, 1979, vol. 98, pp. 388-393.

Lin et al., Amperometric biosensor based on coentrapment of enzyme and mediator by gold nanoparticles on indium-tin oxide electrode, *Analytical Biochemistry*, 2007, vol. 370, pp. 180-185.

Marquez et al., "Mechanism of the Oxidation of 3,5,3',5'-Tetramethylbenzidine by Myeloperoxidase Determined by Transient- and Steady-State Kinetics," *Biochemistry*, 1997, vol. 36, pp. 9349-9355.

Micheli et al., "An electrochemical immunosensor for aflatoxin M1 determination in milk using screen-printed electrodes," *Biosensors and Bioelectronics*, 2005, vol. 21, pp. 588-596.

Petit et al., Preparation and characterization of a new enzyme electrode based on solid paraffin and activated graphite particles, *Talanta*, 1995, vol. 42, pp. 1783-1789.

Volpe et al., "3,3',5,5'-Tetramethylbenzidine as electrochemical substrate for horseradish peroxidase based enzyme immunoassays. A comparative study," *Analyst*, 1998, vol. 123, pp. 1303-1307.

Wang et al., "Direct electrochemisty and electrocatalysis of hemoglobin immobilized on carbon paste electrode by silica sol-gel film," *Biosensors and Bioelectronics*, 2004, vol. 19, pp. 1269-1275.

Wang et al., "Hydrogen peroxide biosensor based on direct electrochemistry of hemoglobin immobilized on carbon paste electrode by a silica sol-gel film," *Sensors and Actuators B*, 2004, vol. 99, pp. 50-57.

British Search Report in British Patent Application No. 0820817.5; dated Mar. 6, 2009.

International Search Report in International Application No. PCT/GB2009/002664; dated Mar. 9, 2010.

Written Opinion of the International Searching Authority in International Application No. PCT/GB2009/002664; dated Mar. 9, 2010.

\* cited by examiner

ELECTRODE, ELECTROCHEMICAL SENSOR AND APPARATUS, AND METHODS FOR OPERATING THE SAME

RELATED APPLICATION

This application claims priority to GB 08208175.5 filed 13 Nov. 2008, the contents of which are hereby incorporated by reference in their entirety.

TECHNICAL FIELD

This invention pertains generally to processes, uses, and methods utilising an electrode, a sensing device, and a sensing apparatus and a sensing system. The invention is particularly, but not exclusively, concerned with gathering biomedical data and/or information.

BACKGROUND

Some disorders of the gastrointestinal (GI) tract are difficult to detect and present detection systems having a camera sensor incorporated into a swallowable pill are often not sufficiently accurate to allow early identification of a problem. Bleeding in the GI tract is a common symptom of several diseases such as Crohn's disease, ulcerative colitis, ulcers and cancer. Bleeding in the GI tract can go unnoticed until it reaches a scale where other symptoms appear, e.g. anaemia, or if fresh blood appears in the stool. By this time, the disease has usually reached an advanced stage. In the case of bowel cancer, polyps often bleed before they become cancerous. Consequently, if they can be detected early, the polyps can be safely removed and the cancer treated successfully. There are known faecal occult blood (FOB) tests, for testing for the presence of blood in stool. These are generally based on the peroxidase-like behaviour of haemoglobin or are based on immunoassays.

One known FOB test uses a guaiac resin impregnated card. Guaiac resin (extracted from trees) changes colour in the presence of oxidising agents. Such tests utilise the fact that haemoglobin catalyses the oxidation of the phenolic compound in guaiac resin (alpha guaiaconic acid) by hydrogen peroxide to form a highly conjugated blue quinone compound. In guaiac-based FOB tests samples of stool are spread by the patient on a card impregnated with guaiac resin. Two samples from each of three stools are typically required to be collected before the card is sent for analysis. In the analysis laboratory, a hydrogen peroxide developer solution is applied to the card and, if blood is present in the sample, a blue-green colour is the result.

The FOB test described above is of use in screening tests, where patients receive the test through the mail, or from their local doctor, take and apply their own samples to the card, and return the card to the laboratory for analysis. The take-up of such tests is variable, particularly amongst the elderly, and amongst people from certain ethnic or social backgrounds, probably due to the unpleasant nature of taking the samples and applying them to the cards.

As an alternative to the screening cards described above, WO 2006/085087 discloses a sensing apparatus, which includes a swallowable pill, having an array of sensor elements, where each element is a biological sensor for detecting the presence of the same analyte in the environment in which the sensor array is to be deployed. Activation of a sensor element in the array allows analyte present in the environment of the sensor element, such as haemoglobin, to catalyse a chemical reaction between a first reagent, such as alpha guaiaconic acid, and a second reagent, and the detection of the chemical reaction by the sensor element determines the sensor element output. The first reagent is typically contained within a reagent space of the sensor, which is covered, and may be made available, as required, by removal of that cover to expose the reagent to the local environment.

The provision of a sensor having a reagent space with a removable cover complicates the design of the swallowable pill. There is need for an alternative sensor having a design that is easier to operate and easier to fabricate.

The present invention is particularly useful in systems where a swallowable capsule with a sensor is swallowed by a patient and transmits gathered data from inside the body to a base station outside the body via a radio or other communication link. However it is not limited to this application and may also be used on a sensing device designed for implantation into the human body. It may also be used in topical application, e.g. in wound dressings. It may also be used with animals, especially but not limited to agricultural livestock, such as cattle sheep and pigs. Application not only to mammals, but also to non-mammals, e.g. fish at fish farms, would also be possible.

The present invention also finds use in the analysis of samples taken from a subject. An analytical device with a sensor may be used for rapid, qualitative measurements of a sample, especially with a view to determining the presence of a protein, such as haemoglobin, at physiological or clinical levels.

Whilst some aspects of the present invention relate to apparatus such as swallowable pills, other aspects provide improved sensors for use in the analysis of biological samples. These sensors may be used as alternatives to those sensors, such as the cards discussed above, that are currently on the market. The sensors of the invention provide faster results without the need for a suitably experienced analytical technician.

SUMMARY OF THE INVENTION

The present invention takes the form of three related developments, an electrode, an electrochemical sensor and a sensing apparatus, as set out below. For each development, there are several aspects. It is to be understood that it is possible to combine aspects of any development with each other, unless the context demands otherwise. Similarly, it is possible to combine preferred and/or optional features singly or together with any of the aspects of any development, unless the context demands otherwise.

In a first aspect the present invention provides an electrode for use in the detection of a protein, the electrode comprising:
 a working electrode having an electrically conductive carbon- or graphite-containing matrix holding a first reagent and a second reagent, the second reagent being an oxidising agent or a precursor thereof for the first reagent,
 wherein a reaction between the first reagent and the oxidising agent is catalysable by the protein to provide a detectable signal at the working electrode.

In a second aspect the present invention provides an electrode for use in the detection of a protein, the electrode comprising:
 a working electrode having an electrically conductive porous matrix holding a first reagent and a second reagent, the second reagent being an oxidising agent or a precursor thereof for the first reagent, wherein a reaction between the first reagent and the oxidising agent is catalysable by the protein to provide a detectable signal at the working electrode.

In a third aspect, the present invention provides an electrochemical sensor comprising an electrode of the invention, and further comprising a counter electrode, and optionally a reference electrode.

In a fourth aspect, the present invention provides a sensing apparatus comprising at least one electrochemical sensor of the invention, wherein the apparatus is adapted:

(i) for use with a sample from a subject;
(ii) to be swallowable, for passage through the human or animal body;
(iii) to be implantable in the human or animal body; or
(iv) to be placed at a surface location of the human or animal body.

In a fifth aspect, the present invention provides a method for detecting a protein, the method comprising the steps of:

(i) providing an electrochemical sensor, the electrochemical sensor comprising:
   a working electrode having an electrically conductive matrix holding a first reagent and/or a second reagent, the second reagent being an oxidising agent or a precursor thereof for the first reagent;
   a counter electrode and optionally a reference electrode;
   wherein a reaction between the first reagent and the oxidising agent is catalysable by the protein to provide a detectable signal at the working electrode; and
   the electrically conductive matrix is an electrically conductive carbon- or graphite-containing matrix or an electrically conductive porous matrix;
(ii) deploying the electrochemical sensor at an environment to be analysed for the protein;
(iii) making available for reaction the first reagent and the second reagent;
(iv) maintaining a potential across the working electrode and the counter electrode and/or the reference electrode, where present; and
(v) measuring the current passing between the working electrode and the counter and/or reference electrode where present.

In a further aspect of the invention there is provided a method of preparing an electrode, an electrochemical sensor or a sensing apparatus of the invention. The invention also provides the use of an electrode, as described above, in a sensor for the detection of a protein.

Figure 14:
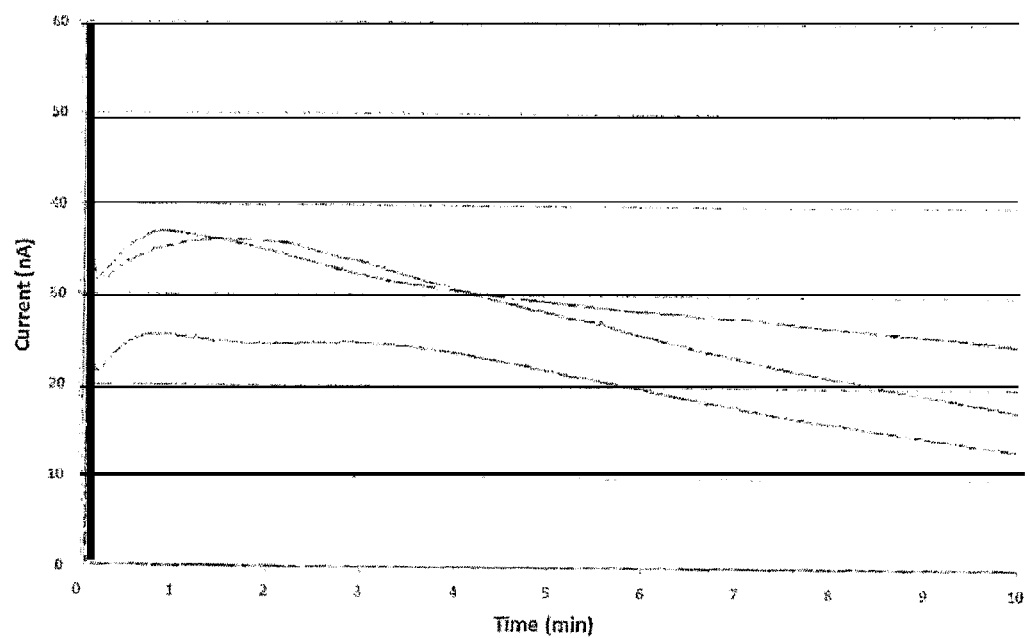

FIG. 14 shows the response curves recorded at a series of TMB-containing carbon paste working electrodes used to electrochemically analyse samples comprising 0.1×Buffer A, URP and Hb. The baseline curve is the response curve relating to the control sample having no Hb present.

Figure 15:
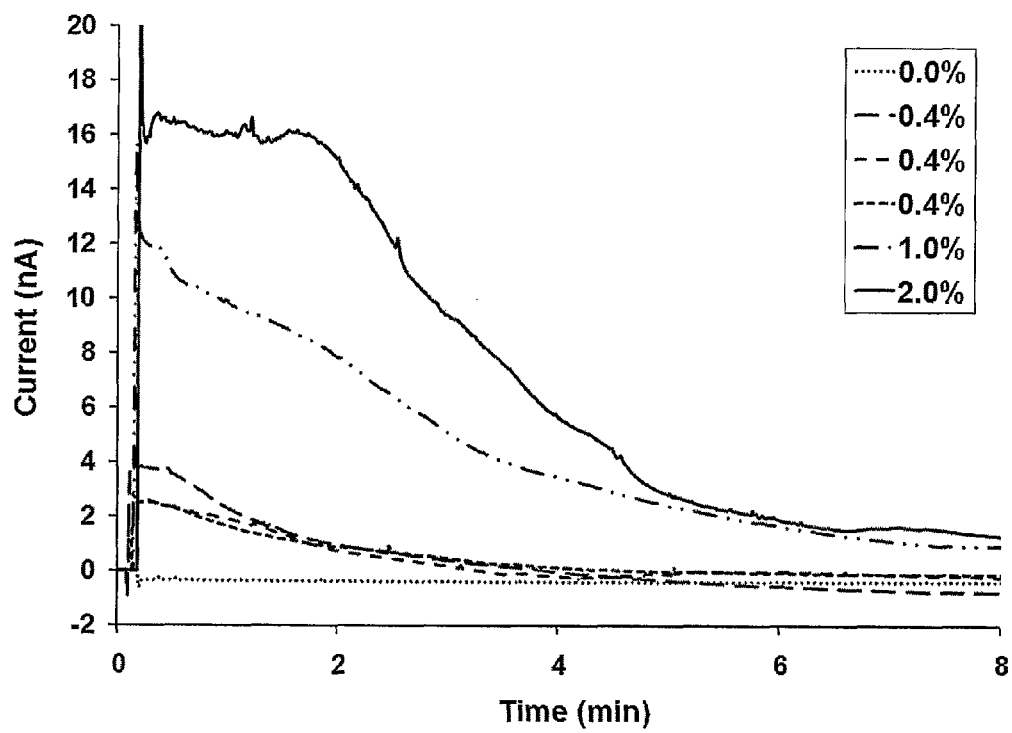

FIG. 15 shows the current recorded at TMB- and sodium perborate-containing carbon paste electrodes over time against a simulated stool sample comprising varying amounts of blood added to condensed illeal effluent. The response curves, from top to bottom, are for samples comprising 2.0 wt % blood, 1.0 wt % blood, and three samples each comprising 0.4 wt % blood. The baseline curve is the response curve relating to a control sample having no blood present.

Figure 16:
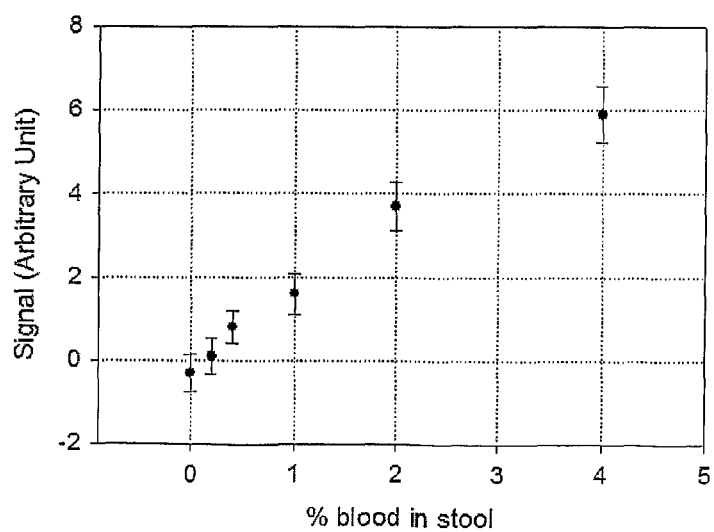

FIG. 16 is a graph showing the mean current density, expressed as an arbitrary unit, calculated from measurements recorded at TMB- and sodium perborate-containing carbon paste electrodes with respect to a variety of simulated stool samples comprising increasing amounts of blood. The mean current density values were calculated from the response curves for each sample.

Figure 17:
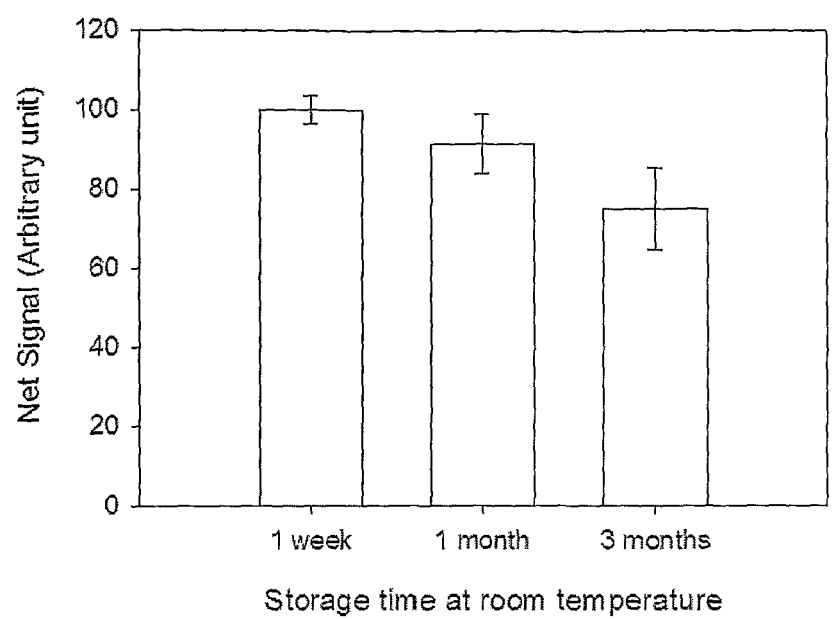

FIG. 17 shows the average change in net signal level, expressed as an arbitrary unit, over time for a carbon paste electrode with TMB and sodium perborate tested against a sample comprising 0.3 mg/mL Hb in 1×Buffer A.

DETAILED DESCRIPTION OF THE INVENTION

The present invention provides an electrode for use in detecting a protein in an environment. The protein catalyses a reaction between a first reagent and a second reagent to provide a detectable signal at the electrode.

In a preferred embodiment, the first reagent and the second reagent are held in an electrically conductive matrix of the electrode.

In an alternative embodiment, one of the first reagent and the second reagent is held in the electrically conductive matrix, and, in use, the other is made available for reaction to provide a detectable signal at the electrode.

The protein catalyses the oxidation of the first reagent by the second reagent in the electrode electrically conductive matrix. The oxidised form of the first reagent may then be reduced at the electrode to provide the detectable signal at the electrode.

The electrode may be incorporated into an electrochemical sensor or a sensing apparatus as described herein.

The features of the electrode, sensor and apparatus are described in detail below.

Electrode

In a general aspect, the present invention provides an electrode having an electrically conductive matrix. In one aspect of the invention, there is provided an electrically conductive carbon- or graphite-containing matrix holding a first reagent and/or a second reagent. Preferably, the first and second reagents are present. Alternatively, one of the first or the second reagent is present.

In another aspect of the invention, there is provided an electrically conductive porous matrix holding a first reagent and/or a second reagent. Preferably, the first and second reagents are present. Alternatively, one of the first or the second reagent is present.

The electrode may be referred to as a working electrode.

The electrode of the present invention is stable. It does not degrade substantially over time or degrade substantially on prolonged exposure to the environment at which it is intended to be used. The working electrode may be incorporated into a sensing apparatus, for example a test card and other such diagnostic kits. Furthermore, for in vivo applications of the electrode, non-toxic components may be used thereby minimising the risk of harm to a human or animal test subject. Thus, in certain embodiments, the working electrode of the present invention is especially suitable for use in a sensing apparatus that is a swallowable pill adapted for transit through the gastrointestinal tract.

The electrode of the present invention may be stored for at least 14 days, at least 28 days, or at least 6 months without significant loss of electrode activity. Preferably the electrode is stored for this time in a dry state to minimise degradation. It is preferred that the working electrode, and optionally the other components of the sensor, is stored in an atmosphere of an inert gas, such as nitrogen or argon.

The activity of the electrode may be gauged by electrochemical analysis of a standard sample solution comprising a protein. A loss of electrode activity corresponds to a fall in the average recorded current recorded at the working electrode in comparison to a recorded current at a control working electrode. Preferably, the fall in average recorded current is about 50% or less, about 30% or less, about 10% or less, or about 5% or less.

The environment against which the stability of the working electrode is tested may include a biological sample as described herein. The working electrode may also be tested against a sample approximating the conditions to which the working electrode is intended to be exposed. The sample may be a simulated intestinal fluid, for example, or a simulated stool sample.

Electrically Conductive Matrix

Generally, the working electrode has an electrically conductive matrix holding a first reagent and/or a second reagent. The matrix can be a porous matrix.

The electrode may be an electrically conductive carbon- or graphite-containing matrix.

The electrically conductive matrix is adapted for electrical connection to a voltage supply.

Preferably the electrically conductive matrix is electrically connected to a conducting substrate. Preferably the conducting substrate is metal.

The metal may be, for example, steel or platinum, and may be in any shape, although wires (including coils) are most preferred. In use, the conducting substrate may form the electrical connection between the electrically conductive matrix of the working electrode and a voltage supply.

In a preferred embodiment the conductive matrix is, or is obtained or obtainable, from a graphite or carbon paste.

In an alternative embodiment the conductive matrix is, or is obtained or obtainable, from a carbon- or graphite-containing ink.

Carbon pastes are well known as such in the art. A carbon paste may be prepared from graphite or carbon particles, and an oil.

The oil may be, amongst others, paraffin, mineral oil or silicone oil. A suitable oil includes a mineral oil available from Sigma-Aldrich (see catalogue number M3516, for example).

Suitable graphite or carbon particles include synthetic graphite powder of average particle size <20 μm available from Sigma-Aldrich (see catalogue number 282863, for example).

The paste is prepared by mixing the graphite or carbon particles and oil together, for example using a pestle and mortar.

A graphite or carbon paste may also be prepared by melting paraffin, for example a paraffin wax, in the presence of graphite or carbon. Typically, the paraffin is heated to a temperature in the range 40-50° C. Such techniques are described in Petit et al.

Alternatively, a commercially available paste may be used. A suitable carbon paste includes a carbon paste available from Bioanalytical Systems, Inc. (see, for example, catalogue number CF-1010).

The typical composition for a paste is 55-75 wt % graphite or carbon, and 25-45 wt % oil. Preferably the composition is 60-70 wt % graphite or carbon, and 30-40 wt % oil.

The electrically conductive matrix may be a carbon ink.

A carbon or graphite ink typically has a solids content in the range 30-50 wt %, preferably 33-45 wt %. Carbon or graphite ink commonly includes carbon or graphite with a solvent and a binder, such as a vinyl- or epoxy-based polymeric binder.

Carbon and graphite inks are commercially available, and suitable inks for use in the present invention include those inks from Acheson Colloids (see, for example, Electrodag Standard Carbon Ink PF-407A), Dupont Electronic Materials (see, for example, product number BQ242), Gwent Electronic Materials Ltd (see, for example, product number C10903P14) and Ercon.

The electrically conductive matrix may be multilayered. A multilayered electrically conductive matrix allows the first and/or second reagents, and additional additives where present, to be physically separated within the matrix. This has been found to increase the stability of the matrix in comparison to a matrix having the first and/or second reagents, and additional additives where present, within a single layer.

The multilayered conductive matrix minimises the cross reactivity of the components of the matrix. For example, the cross reactivity of the first reagent and the second reagent in the absence of the protein is reduced in the multilayered conductive matrix.

The multilayered electrically conductive matrix may have a layer of carbon paste or carbon ink that does not hold either the first or second reagent. Preferably this layer consists of carbon paste or carbon ink. Where a conducting substrate is present, it is preferred that this layer of carbon paste or carbon ink is attached to the conducting substrate.

Preferably the matrix has a first layer holding the first reagent and a second layer holding the second reagent, where each of these reagents is present.

In a most preferred embodiment, the electrically conductive matrix comprises a first layer of carbon paste or carbon ink, that layer holding one of the first reagent or the second reagent. Adjacent to the first layer is a second layer of carbon paste or carbon ink, that layer holding the other of the first reagent or the second reagent. Adjacent to the second layer, and on the opposite side to the first layer, is a third layer of carbon paste or carbon ink. The third layer may not hold either the first or second reagent, and preferably consists of carbon paste or carbon ink. Optionally, a conducting substrate may be present adjacent to the third layer, and on the opposite side to the second layer.

It is preferred that the first layer is exposed to an electrolyte space, as described herein. Thus, it is the first layer that is exposable to the environment in use.

It is preferred that the first layer holds the second reagent, and the second layer holds the first reagent.

It is preferred that carbon ink is used in a multilayered electrically conductive matrix.

The electrically conductive matrix is porous. The porous network permits, in use, a protein to penetrate the matrix where it is made available to catalyse the reaction between a first reagent and a second reagent. Where only one of these reagents is present in the electrically conductive matrix, the pores permit, in use, the other of those reagents to penetrate the matrix where it is made available for reaction with the one reagent catalysed by the protein.

Preferably the pores have an average diameter in the range of at least 8 µm, at least 10 µm, at least 15 µm, or at least 20 µm.

Preferably the pores have an average diameter in the range of at most 8 µm, at most 20 µm, at most 25 µm, or at most 30 µm.

Preferably the pores have an average diameter in the range of about 8 to about 30 µm.

The size of pores in an electrically conductive matrix may be determined experimentally by SEM.

First Reagent

The first reagent is reactable with the second reagent in the presence of the protein. Preferably the second agent is hydrogen peroxide. Therefore, the first reagent is preferably a compound that reacts with hydrogen peroxide in the presence of the protein.

Preferably the first reagent is, or comprises, a compound selected from tetramethylbenzidine, alpha guaiaconic acid, 2,2'-azino-bis(3-ethylbenzothiazolidine-6-sulphonic acid), hydroquinone, phenylenediamine, o-dianisidine, o-tolidine (dimethylbenzidine), 6-methoxyquinoline, and 3,3'-diaminobenzidine, 3-amino-9-ethylcarbazole.

Preferably the first reagent is, or comprises, tetramethylbenzidine. Preferably the first reagent is, or comprises, 3,3', 5,5'-tetramethylbenzidine.

In certain embodiments of the invention, the sensor is part of a sensing apparatus that is adapted to be swallowable, for passage through the human or animal body, or to be implantable in the human or animal body, or to be placed at a surface location of the human or animal body (e.g. a wound site). Thus, it is preferred that the components of the sensor are not harmful to the subject into or onto which the apparatus is placed.

For in vivo applications of the electrode, it is preferred that the first reagent is a compound that is not toxic to a subject. Additionally or alternatively, the first reagent is not a compound that is converted to a product that is toxic upon oxidation by the oxidising agent.

In the most preferred embodiment, the first reagent is, or comprises, tetramethylbenzidine. This reagent is particularly suitable for use in the invention as it is not believed to be harmful to human subjects.

The amount of first reagent present in the working electrode is selected to allow the optimal performance of that electrode. The amount of first reagent present is of a quantity sufficient to give rise to a detectable signal upon reaction of that first reagent with the second reagent in the presence of the protein, where the protein is present at physiological or clinical levels. The amount of reagent present is at a concentration that allows sufficient electron transmission through the matrix. The amount of reagent is selected so as to provide optimal sensitivity and response times in use.

Additionally or alternatively, the amount of first reagent present is the amount that gives the optimal structural integrity to the electrically conductive matrix.

The first reagent may be present in the electrically conductive matrix in at least 1 wt %, at least 2 wt %, or at least 5 wt %.

The first reagent may be present in the electrically conductive matrix in at least 4 wt %.

The first reagent may be present in the electrically conductive matrix in at most 15 wt %, at most 9 wt %, or at most 5 wt %.

The first reagent may be present in the electrically conductive matrix in at most 15 wt %, at most 9 wt %, or at most 6 wt %.

Preferably the first reagent is present in the electrically conductive matrix at 1-15 wt %.

Preferably the first reagent is present in the electrically conductive matrix at 2-9 wt %. Preferably the first reagent is present in the electrically conductive matrix at 5 wt %.

Second Reagent

The second reagent is an oxidising agent or a precursor thereof. It is reactable with the first reagent in the presence of the protein.

Preferably the second reagent comprises hydrogen peroxide or a precursor thereof. Preferably hydrogen peroxide is releasable from the second reagent upon contact of the second reagent with water.

The hydrogen peroxide is reactable with the first reagent in the presence of the protein.

Preferably the second reagent is, or comprises, a compound selected from urea peroxide, a perborate compound and a periodate compound. In one embodiment, the second reagent is, or comprises, urea peroxide. In another embodiment, the second reagent is, or comprises, a perborate compound, preferably sodium perborate. For ex vivo applications, sodium perborate is preferred as the resulting electrode has a greater stability than those electrodes comprising other reagents, for example those electrodes comprising urea peroxide. In particular, those electrodes comprising sodium perborate have been found to have a longer shelf-life.

For in vivo applications of the electrode, it is preferred that the second reagent is a compound that is not toxic to a subject. Additionally or alternatively, the second reagent is not a compound that is converted to a product that is toxic upon reaction with the first reagent. Thus, for in vivo applications, urea peroxide is the preferred second reagent owing to its low toxicity.

For ex vivo applications of the electrode, the toxicity of the second reagent is less of a concern. The exposure of the user to the reagent may be minimised by appropriate containment.

The amount of second reagent present in the working electrode is selected to allow the optimal performance of that electrode. The amount of second reagent present is of a quantity sufficient to give rise to a detectable signal upon reaction of that second reagent with the first reagent in the presence of the protein, where the protein is present at physiological or clinical levels. The amount of reagent present is at a concentration that allows sufficient electron transmission through the matrix. The amount of reagent is selected so as to provide optimal sensitivity and response times in use.

Additionally or alternatively, the amount of second reagent present is the amount that gives the optimal structural integrity to the electrically conductive matrix.

The second reagent may be present in the electrically conductive matrix in at least 2 wt % or at least 7 wt %.

The second reagent may be present in the electrically conductive matrix in at least 6 wt %.

The second reagent may be present in the electrically conductive matrix in at most 15 wt %, at most 11 wt % or at most 7 wt %.

The second reagent may be present in the electrically conductive matrix in at most 8 wt %.

Preferably the second reagent is present in the electrically conductive matrix at 2-15 wt %.

Preferably the second reagent is present in the electrically conductive matrix at 7-11 wt %.

Preferably the second reagent is present in the electrically conductive matrix at 7 wt %.

Electrode Additives

The working electrode holds a first reagent and/or a second reagent. The electrode may optionally comprise one or more further additives.

In a multilayered matrix, the additives may be in a layer with the first and/or second reagent, or may be in a separate layer that does not include either the first or the second reagent.

The electrode additives may be included to alter the structure of the electrically conducting matrix. The additives may be included to alter the local environment into which the electrode is placed. For example, an additive may be provided to alter the local pH at and about the working electrode surface.

In some embodiments the additives may be releasable from the electrode upon contact with water, which is typically present in the sample to be analysed. In this embodiment, the electrode is maintained dry until use. Where the electrode is a multilayered matrix, it is preferred that the additive is contained within the layer that is intended to contact the electrolyte.

pH Controlling Additive

In one embodiment the working electrode comprises a pH controlling additive. The additive may be held in the matrix. In use, the pH controlling additive may be released from the electrode into the electrolyte space, thereby altering the pH of the local environment, and particularly the environment about the electrode reactive surface.

It has been determined that the strongest detectable signal at the electrode resulting from the reaction of TMB and URP catalysed by a protein is obtained where the pH of the environment is about pH 5.

Accordingly, where the environmental pH is expected to be greater than pH 5, the electrode may be provided with a pH altering additive to alter the pH of that environment in use. The pH controlling additive may be an acid or a buffer.

The pH altering additive may be released from the electrode into the environment upon contact with a fluid at that environment, for example an intestinal fluid. The pH controlling additive may be releasable upon hydration.

In a single use electrode system, the acid is suitable as a pH controlling additive. The pH controlling additive may be a buffer. In a preferred embodiment, the pH controlling additive is a citrate buffer (citric acid and sodium citrate). In principal any buffer that is a conjugate base of an organic acid may be used. Examples include acetate and phosphate buffers, and combinations thereof. Other buffers suitable for use include MOPS, CHAPS, TRIS, and HEPES buffers.

The buffer is preferably not toxic to a subject.

The amount of first reagent present in the working electrode is selected to allow the optimal performance of that electrode. The amount of buffer present is at a concentration that allows sufficient electron transmission through the matrix.

The pH additive may be present in the electrically conductive matrix in at least 1 wt %, at least 2 wt % or at least 5 wt %.

The pH additive may be present in the electrically conductive matrix in at most 15 wt %, at most 9 wt % or at most 5 wt %.

Preferably the pH additive is present in the electrically conductive matrix at 1-15 wt %. Preferably the pH additive is present in the electrically conductive matrix at 2-9 wt %. Preferably the pH additive t is present in the electrically conductive matrix at 5 wt %.

In a preferred embodiment, the working electrode holds a first reagent and/or a second reagent, mannitol and a citrate buffer.

Pore-Forming Additive

In one embodiment the working electrode comprises a pore-forming additive. The additive may be held in the the matrix. The additive may increase the size and/or number of pores within the electrode matrix. It has been determined that the strongest detectable signal at the electrode results from the reaction of the first reagent and second reagent catalysed by the protein in a matrix having an increased size and/or number of pores.

The pore-forming additive may also be used to more evenly distribute the pores within the matrix, thereby allowing, in use, the protein to penetrate further or more rapidly into the matrix.

Preferably the pore-forming additive is a polyol.

Preferably the pore-forming additive is independently selected from sodium sulfate, mannitol, sorbitol and xylitol.

Preferably the pore-forming additive is independently selected from mannitol, sorbitol and xylitol. Most preferably the pore-forming additive is independently mannitol.

Alternatively, the pore-forming additive is sodium sulfate. Sodium sulfate is particularly preferred where the electrode comprises a pH controlling additive such as citric acid.

In another embodiment, the pore-forming additive is sodium bisulfate. Sodium bisulfate may be used in preference to mannitol where pH control of the sample is required, in particular where it is preferred that the sample is at acidic pH during the electrochemical analysis. Sodium bisulfate is preferred over mannitol owing to its lower pKa (about pka 2 compared to pka 13.1 and 13.8 for mannitol).

The pore-forming additive may be present in the electrically conductive matrix in at least 1 wt %, at least 10 wt %, at least 20 wt %, or at least 30 wt %.

The pore-forming additive may be present in the electrically conductive matrix in at most 55 wt %, or at most 45 wt %.

Preferably the pore-forming additive is present in the electrically conductive matrix at 1-50 wt %.

Preferably the pore-forming additive is present in the electrically conductive matrix at 35-45 wt %.

Preferably the pore-forming additive is present in the electrically conductive matrix at 40 wt %.

Wetting Additive

In one embodiment the working electrode comprises a wetting additive. The wetting additive may be held in the matrix.

The wetting additive may be used to accelerate the hydration of the matrix, in use, thereby providing increased response times.

The wetting additive is preferably non-ionic.

Preferred wetting additives include polyvinylpyrrolidone, Triton X, and tween.

The wetting additive may be present in the electrically conductive matrix in at least 0.005 wt %, at least 0.01 wt %, or at least 0.05 wt %.

The wetting additive may be present in the electrically conductive matrix in at most 0.50 wt %, at most 0.25 wt %, or at most 0.1 wt %.

Preferably the wetting additive is present in the electrically conductive matrix at 0.005-0.25 wt %.

Preferably the wetting additive is present in the electrically conductive matrix at 0.01-0.1 wt %.

Electrode Modification

In one embodiment, the electrode has a coating over at least part of its surface. The material coating the electrode is preferably soluble in the sample to be tested. Thus, on contact with a sample, the coating is removed by dissolution from the electrode. The coating is preferably removable upon hydration.

The coating may be in the form of a matrix to permit permeation of the sample solution throughout the coating, thereby aiding dissolution from the electrode surface.

The coating is provided to hold one or more additives, such as those electrode additives described above. The coating may be used as an alternative, or in addition to, the electrodes described above where the additives are held within the electrode matrix. The coating is not required to be electrically conductive as the coating is at least partially removed prior to electrochemical analysis, thereby ensuring that a part of the electrode surface is available for contact with the sample.

In a preferred embodiment, the electrode coating has a pH controlling additive, such as those described above. In this embodiment, it is preferred that the electrode does not contain a pH controlling additive.

Preferably, the coating material is, or comprises, a water-soluble polymer. Suitable water-soluble polymers include those polymers that are used in the pharmaceutical field in drug-release systems.

Water-soluble polymers for use in the present invention include one or more of the following polymers and derivatives thereof: polyalkylene glycol, for example polyethylene glycol; cellulosic polymers, for example hydroxyalkylcellulose including hydroxyethylcellulose and hydroxypropyl methylcellulose; sucrose or other polysaccharides, for example chitosan; and vinyl polymers, for example poly(vinylpyrrolidone) and poly(vinylpyrrolidone)-(vinyl acetate) copolymer.

Preparation of a Working Electrode

The present invention also provides methods for the preparation of working electrodes.

Thus, in one aspect, there is provided a method of preparing a working electrode, the method comprising the step of mixing a carbon- or graphite-containing matrix with a first reagent, a second reagent, or both. The carbon- or graphite-containing matrix is preferably a carbon- or graphite-paste, or a carbon- or graphite-ink.

Preferably the first reagent, the second reagent, or both reagents are independently ground prior to mixing with the carbon- or graphite-containing matrix.

Preferably the first reagent, the second reagent, or both reagents are independently ground then combined by vortexing prior to mixing with the carbon- or graphite-containing matrix. The resulting blend may be homogenised in a mortar, and then vortexed. The process may be repeated until a paste of desired uniformity is obtained.

In some embodiments of the invention the electrode has a removable coating over at least part of its surface. The coating may be deposited onto the outer surface of the electrode from a solution of coating material in an organic solvent. The solvent may be evaporated leaving a film of material on the electrode surface. Alternatively, the coating may be applied by dissolving or dispersing coating material in an organic solvent, and then spraying the resulting mixture on to the electrode. This technique is similar to the film coating techniques used in the pharmaceutical industry to coat a pharmaceutical composition with, for example, a water-soluble polymer.

In some embodiments, the electrode may be retained within a cavity of, for example, a sensing apparatus. In this embodiment, the coating material may be packed into the cavity, thereby at least partially covering the electrode within the cavity. Upon hydration, the coating material dissolves exposing the previously covered electrode portions to the sample.

The present invention also provides a working electrode obtained or obtainable by the methods described herein.

Electrochemical Sensor

The electrochemical sensor of the invention comprises an electrode of the invention along with a counter electrode and optionally a reference electrode.

The working electrode, counter electrode and optionally the reference electrode, define an electrolyte space. In use, the electrodes are in electrical contact with electrolyte in the electrolyte space.

For qualitative measurements, a reference electrode may not be required.

Preferably, activation of the sensor allows analyte (i.e. protein) present in the environment of the sensor elements, particularly the working electrode, to catalyse a chemical reaction between a first reagent and a second reagent, detection of said chemical reaction by said sensor element determining the sensor output.

The electrodes are adapted for electrical connection to a voltage supply.

The electrochemical sensor may be activatable only once to attempt to detect the presence of the analyte at the environment to which the sensor is deployed.

The activation of the electrochemical sensor allows the analyte present at the environment of the electrochemical sensor to catalyse a chemical reaction between the first reagent and the second reagent, the detection of this chemical reaction by the electrochemical sensor determining the electrochemical sensor output.

Working Electrode

The electrochemical sensor comprises a working electrode having an electrically conductive matrix as described herein.

The working electrode is exposable to the environment to be analysed for protein. Preferably the working electrode is exposable upon activation of the electrochemical sensor.

Counter Electrode

The electrochemical sensor comprises a counter electrode. The counter electrode is connectable to a power source. Preferably, the counter electrode is connected to the power source when the counter electrode is used as a reference electrode.

There are no specific limitations on the type of counter electrode that may be used in the electrochemical sensor of the invention. Preferred electrode materials include steel and platinum. Steel is the most preferred electrode material for use in disposable and one shot sensors and apparatus owing to its relatively low cost.

Reference Electrode

A reference electrode may be included in the electrode device of the invention.

The working electrode and the counter electrode, along with the reference electrode and further working electrode where present define an electrolyte space. In use, the electrodes are in electrical contact with an electrolyte in said electrolyte space. The electrolyte may be a sample as described herein, or may be the fluid at the environment to which the sensor is delivered.

The reference electrode may be a standard silver/silver chloride electrode. The reference electrode may be a pseudo reference electrode, which is operable as a reference electrode in the presence of a suitable buffer comprising appropriate ions. In one embodiment, the pseudo reference electrode may be a silver-based electrode that is obtained, or is obtainable from, a silver electrode that is treated with about 1% aqueous $FeCl_3$ solution. The electrode may be washed before and/or after the treatment.

Additional Working Electrode

The electrochemical sensor may comprise a second electrode. The additional working electrode may be the same or different to the first working electrode.

The second working electrode may be provided to permit differential electrochemical measurements to be taken in the use of the electrochemical sensor. The second working electrode may be used in permit duplicate electrochemical measurements to be taken in order to demonstrate accuracy and increase confidence.

The sensor of the invention may be provided in a triplicate or quadruplicate configuration. Thus, the sensor may include two or three further working electrodes.

The addition of a further electrode can improve the overall performance of the electrochemical sensor by allowing a higher specificity for the protein. Thus, the electrode is more capable of discriminating between different types of proteins, for example, between haemoglobin and horseradish peroxidase.

In one embodiment, the second working electrode is provided to measure the uncatalysed reaction between the first and second reagent. In this embodiment, the electrochemical sensor is provided with means for reducing, or preventing in use, exposure of the second working electrode to the protein.

The means may be a membrane. The membrane is impermeable to the protein. The membrane may be referred to as a semi-permeable membrane, as the membrane is intended to permit, in use, the passage of other components in a sample across the membrane. These other components may then have access to the second working electrode.

In one embodiment, the other components are peroxide scavengers, that is compounds that are known to react with peroxide. Such compounds include, but are not limited to, ascorbate (or ascorbic acid) and urate (or uric acid). Such compounds may be permitted to pass through the membrane and contact and pass into the electrode matrix. The other component may react at the electrode, for example with the first or second reagent, to give rise to a detectable signal at the second working electrode. The signal arising from this (non-specific) reaction may be used to calibrate or correct the signal obtained from the (specific) protein-catalysed reaction at the first working electrode.

The membrane may have through pores of a dimension sufficient to prevent passage of the protein across the membrane. This may be referred to as size exclusion.

Preferably the pores have an average cross-section of 5 µm or less, 4 µm or less, 1 µm or less, or 0.5 µm or less.

Membranes are commercially available, and suitable membranes for use in the present invention include membranes from Millipore (for example, Millipore Immobilon-P Membrane, Millipore Fluoropore PTFE, Millipore Durapore PVDF, and Millipore Isopore track-etched polycarbonate), Sterlitech (for example, Sterlitech Corp polyester membranes and track-etched polycarbonate membrane filters) and Whatman (for example, Whatman track-etched polycarbonate membrane filters).

Electrochemistry

The electrochemical sensor may further comprise a voltage supply (or power supply). The voltage supply is preferably adapted to supply a constant bias between the working electrode and the counter electrode or the reference electrode, where present.

Preferably the voltage supply is adapted to supply a constant bias in the range −0.05 to +0.25 V between the working electrode and the reference electrode or counter electrode.

Preferably the voltage supply is adapted to supply a constant bias of about +0.10 V between the working electrode and the reference electrode or counter electrode.

The electrochemical sensor may further comprise a detector for monitoring current. The electrochemical sensor may further comprise a controller for controlling the voltage supply and timing of that supply.

Alternatively the voltage supply and/or the controller may be provided externally. In one embodiment the voltage supply and/or the controller may be a component of an apparatus, such as those apparatus described herein, and in particular as a component of a first module of the apparatus as described herein.

This is particularly preferred where the apparatus, or the first module of the apparatus, comprises an array of electrochemical sensors of the invention. One or more, or each, of the electrochemical sensors of the array may be supplied from a common voltage supply and/or may be controlled by a common controller.

The electrochemical sensor may be provided with reagents to improve the detection of a signal at the working electrode. This reagent is releasable into the electrolyte space. The reagent may be released upon activation of the electrochemical sensor. The reagent may be held in a reservoir, which may include a gel, which is located adjacent or close to the working electrode.

The reagent may be selected from those electrode additives described above. Thus, the reservoir may be used in addition, or as an alternative to, those electrodes comprising such additives and/or those electrodes having a coating comprising such additives.

The reservoir may release a reagent upon contact with a sample. The reservoir material may, at least in part, be soluble and is preferably soluble upon hydration, thereby to release the reagent into the sample. The reservoir is preferably composed of a water-soluble polymer. Suitable water-soluble polymers are those polymers described herein for use as a coating material for the electrode.

The reservoir is preferably located in close proximity to the working electrode (or working electrodes, where such additional electrodes are provided). The reservoir may be located adjacent the electrolyte space. A reagent contained within the reservoir may therefore be made available to the electrode working surface prior to and during electrochemical analysis.

In one embodiment, the reservoir contains a pH controlling additive, such as those described above. In this embodiment, it is preferred that the working electrode does not contain a pH controlling additive.

In a preferred embodiment the reagent is a pH controlling additive, such as those additives described above. In another embodiment, the reagent is a wetting additive, such as those additives described above.

Sensing Apparatus

The present invention provides a sensing apparatus having at least one electrochemical sensor of the invention. The components of the electrochemical sensor of the present invention are suitable for miniaturisation. Apparatus having a sensor may likewise be compact. Thus, the sensing apparatus may be a device adapted for passage through the gastrointestinal tract, or it may be a test card or other such test system, suitable for use in a home test kit.

In one embodiment, there is provided a sensing apparatus adapted to analyse a sample from a subject. The sensing apparatus may be a handheld device and may be adapted for use by a user who is not a clinician or a qualified technician. The apparatus may be provided for use by a private individual as part of a home test kit.

In a preferred embodiment, the sensing apparatus is provided as part of a kit including a sampling apparatus suitable for storing and/or sampling a biological specimen from a subject. The kit may optionally further include instructions which may relate to the use of the sensing apparatus, the use of the storing and/or sampling apparatus, and the interpretation of the sensing apparatus results. The sampling apparatus may be integral with the sensing apparatus and may be removable therefrom. Thus, in this embodiment, there is provided a single piece of equipment for sampling and analysing a sample.

In a preferred embodiment, the sampling apparatus is adapted for the removal of a stool sample from a stool.

In one embodiment, the sensing apparatus comprises the electrochemical sensor and the sensor is adapted for contact with and electrochemical analysis of the sample. The sensor may be formed as a test card, for example, or alternatively the sensor may have a more complex architecture and may be formed as a sampling head.

In another embodiment of the invention the apparatus comprises an electrochemical sensor formed as a test card.

In these embodiments, it is particularly preferred that the electrodes of the invention are adapted for use in or on a card. Thus, the thickness of each electrode is relatively small, preferably 10 mm or less, 5 mm or less, or 1 mm or less. In these embodiments it is particular preferred that the working electrode comprises an electrically conductive carbon-ink matrix.

The electrochemical sensor may be used to test a sample for the presence of a protein. It is preferred that the protein is haemoglobin. The electrochemical sensor may therefore be used to test for the presence of blood or a degradation product of blood in that sample.

In some embodiments, the electrochemical sensor in the sensing apparatus comprises the first and second reagents. The reagents may be contained within the working electrode, or one of the reagents may be contained in the working electrode and the other may be provided in a reagent space of the working electrode and may be made available for reaction with the other reagent upon activation of the sensor.

In other embodiments, the electrochemical sensor in the sensing apparatus comprises one of the first and second reagents. The other of the first and second reagents is provided separately, for example added to the sample solution to be analysed.

The sensing apparatus may be disposable. In one embodiment, the sensing apparatus is a single use apparatus. In other embodiments, the sensing apparatus is adapted for multiple use. In this embodiment, the electrode may be provided with a quantity of first and/or second reagent sufficient for multiple use, or the analysis unit may be provided with more than one working electrodes, as described below.

The sensing apparatus is not limited in shape, size or construction. Preferably the sensing apparatus is adapted for use with a biological sample, and is adapted for use in electrochemical analysis of that sample. In one embodiment the sensing apparatus is in the form of a body suitable for holding by hand.

The sensing apparatus may be adapted to give a visual or audible signal to the user upon completion of the electrochemical analysis. This signal may indicate to the user the absence of the protein, the presence of the protein at physiological levels or the presence of the protein at clinical levels. The signal may be in the form of a colour mark, which may change, or the appearance of a mark at a particular marked location on the card which is indicative of a certain result.

In a preferred embodiment, the apparatus is provided with an electronic display which is capable of providing a visual indicator as to the result of the analysis. The indicator may be a word and/or a symbol. The electronic display provides greater certainty as to the result displayed, and the display is not susceptible to subjective interpretation. Such interpretation is a particular disadvantage of tests where a positive result is indicated as a colour change. The change may be difficult to visualise, and may not be uniform, thereby providing an inconclusive or uncertain result to the user.

The sensing apparatus may be used to indicate the presence of a protein over a series of tests. Repeat experiments minimise the chance of false positive results. The sensing apparatus may be adapted for a series of repeat experiments. Thus the sensing apparatus may have a sensor that is usable two or more times. Alternatively, the apparatus may be provided with two or more sensors, where each sensor is provided for one of the series of experiments.

The sensing apparatus may be further provided with an alarm that indicates to a user when a further test on a new sample should be performed. The alarm may be a visual or audible alarm or both.

The sensing apparatus may also be provided with a counter to indicate the number of tests taken and/or the number of tests remaining.

The sensing apparatus may be supplied as part of a kit, which may further comprise a test solution. The test solution may be provided for mixing with a sample to give a more suitable electrolyte for analysis. The test solution may be a buffer solution.

Where the electrochemical sensor is not provided with one of the first and second reagents, that reagent may be provided as part of the kit. The reagent may be supplied in the test solution, or in a separate reagent solution for addition to the test solution. In other embodiments, certain additives, which may be the same as the electrode additives described herein, may be supplied in the test solution, or in a separate reagent solution for addition to the test solution.

In these embodiments, the kit may be referred to as having dry and wet chemistry elements. The dry element of the kit refers to components that are held in the electrode matrix, including the first and/or second reagents. The wet element of the kit refers to the components that are provided as a test solution, such as one of the first and second reagents and/or a diluent, for addition to the sample prior to electrochemical analysis. The wet chemistry element may also refer to those components of the apparatus which are intended to be made up into a test solution, for example by the addition of water. Thus, the wet chemistry components may be provided as solids or gel for make-up into a test solution. The wet and dry elements may be provided separately, for example in different kits.

In a preferred embodiment, the sensing apparatus is provided as part of a kit which also includes a wet chemistry element. The wet chemistry element may be a diluent as described herein, or a mixture suitable for generating a diluent, for example by addition of water. In these embodiments the sensing apparatus preferably comprises a working electrode having the first and second reagents.

The kit may include a set of operating instructions. The operating instructions may be in paper form, on an electronic carrier or available or downloadable from a website, whose address is provided.

In another embodiment of the invention, there is provided an apparatus having a removable working electrode. After use, the first and/or second reagent in the working electrode may be exhausted, or at such a low level as not to allow a detectable signal to be recorded at the working electrode. Hence the present invention provides an apparatus where a spent working electrode may be replaced with a new working electrode. Such a device is particularly useful with single use working electrodes. The working electrode may be replaced as required, whilst other more expensive and complex components of the sensor, such as the power supply, control electronics, and visual display, where present, may be retained in the apparatus for use with a replacement working electrode.

In one embodiment, the working electrode, optionally together with a counter electrode, a reference electrode and other working electrodes where present, is removable from the apparatus together with the sample. The sample may be removable with a sample reservoir. After removal, a new working electrode, optionally together with a new counter electrode, a new reference electrode and other new working electrodes where present, may be subsequently added to the apparatus. A new sample reservoir may also be added.

The working electrode optionally together with one or more of the counter electrode, a reference electrode, and other working electrodes where present may be in the form of a cartridge adapted for placement in and removal from an apparatus. The sample reservoir may be a component of the cartridge.

The apparatus of the invention may be provided with additional sensors. The sensors may be further biological sensors intended to provide additional information regarding the presence or absence of certain analytes at the environment. The sensors may help in the analysis, and ultimately diagnosis, of a subject.

Additional sensors may also be provided in order to control the electrochemical sensor of the invention. For example, a temperature or pH sensor may be provided alongside the sensor of the invention. Once the temperature or pH of the local environment reaches a threshold level, as detected by the temperature or pH sensor respectively, these sensors may activate the electrochemical sensor.

Suitable sensors for use in the apparatus of the invention are described in WO 2006/085087.

In one embodiment, the sensing apparatus includes a first module and a second module, said first module having a controller, a transmitter and one or more electrochemical sensors, said controller being capable of activating one or more of the electrochemical sensors, said transmitter being configured to transmit electrochemical sensor data, derived from said electrochemical sensor output, from said first module to a receiver of said second module, wherein each electrochemical sensor is a biological sensor for detecting the presence of a protein in the environment at which the electrochemical sensor is to be deployed.

Where there are two or more electrochemical sensors present in the first module, the controller is capable of activating one or more electrochemical sensors in said array independently of others in the array, in order to obtain a sensor output from said array at different times by using different electrochemical sensors in said array.

In one embodiment the first module is adapted to be:
  (i) swallowable, for passage through the human or animal body;
  (ii) implantable in the human or animal body; or
  (iii) placed at a surface location of the human or animal body (e.g. at a wound site).

The first module may be in the form of a capsule, which is suitable for transport through the gastrointestinal tract.

For application (i), this places limits on the physical dimensions and shape of the first module. With respect to the shape, typically the first module is elongate with an aspect ratio of 2.5:1 or more, preferably 3:1 or 4:1 or more. Of course, the particular size is dependent on the GI tract through which the first module should pass. For application (ii), there are fewer general limits placed on the size or shape of the first module. However, for both (i) and (ii), the first module should be formed of biocompatible and/or nontoxic materials. For application (iii), it is preferred that the first module has a flat form, optionally a flexible form. For example, the first module may be provided at a wound site on the body, preferably on or within a wound dressing.

The first module may comprise an array of electrochemical sensors. Each sensor may be independently operable.

Each sensor may be activated at a different time to the other sensor in the array. Thus the apparatus may be used to obtain readings as that apparatus passes through the GI tract. The time of the activation may be set according to the predicted transport of the apparatus through a particular segment of the tract.

Preferably, each sensor is activatable only once to attempt to detect the presence of an analyte in said environment In this way, it is preferred that each sensor is only capable of operation once. Typically, this is because the sensors rely on a chemical reaction using at least one reagent, the use of the reagent in a sensor element for a measurement meaning that the sensor element cannot carry out a further measurement.

Preferably, the sensor output corresponds to an analyte condition of at least one of: analyte present; analyte not present; a quantitative measure of the concentration of analyte detected. Thus, each sensor may be capable of providing a measure of concentration of the analyte. However, in certain embodiments, it may be sufficient that each sensor element is capable only of determining whether the analyte concentration is above a certain threshold (analyte present) or below a certain threshold (analyte not present). Preferably, said analyte is blood, or haemoglobin, or another component of blood or a degradation product of blood. Alternatively, the analyte may be other body fluids or components thereof, such as lumen, digestive enzymes, food or the products of food digestion, or wound fluid.

The first module may include means for transmitting the data recorded by the electrochemical sensor from inside the body to a base station outside the body via a radio or other communication link.

The electrode space of the electrochemical sensor is exposable to the sample or the environment upon activation of the sensor. Each sensor may include a cover member for covering the electrode space, the cover member being at least partially removable to allow exposure of the electrode space. Preferably, the cover member is at least partially removable by application of an electrical voltage to the cover member. The electrical voltage may trigger at least one of: corrosion, dissolution, melting, sublimation and breakage of that cover member. The cover member is capable of protecting the electrode from reactive physiological fluids. Such fluids may degrade the electrode matrix material, or may react with the first or second reagent to deplete the electrode of these materials. Thus, the cover prevents fluid access to the electrode surface until required.

Preferably, the electrochemical sensor is provided at an outer surface of the apparatus, so as to be provided in contact with the environment in which the apparatus is to be deployed. In this way, each sensor element may be directly exposed to the environment (at least at the time of activation) without requiring fluid from the environment to travel along channels or conduits in the device. This is particularly preferred, since some regions of the GI tract (e.g. the colon) have contents that are substantially solid and compacted, and thus difficult to flow.

Preferably, the first module is a radio transmitter and the second module's receiver is a radio receiver.

In one embodiment, the first module is a swallowable capsule or an implant device for insertion into the large bowel having an aperture for allowing passage of body fluids.

In one embodiment, the first module has an exterior casing with one or more grooves for channelling fluids towards one or more openings in the exterior casing.

In one embodiment, the first module is a swallowable capsule and comprises an exterior casing having at least one helical groove, protrusion or indentation for causing the capsule to rotate as it passes through the intestinal tract.

Use of the Electrode, Electrochemical Sensor and Sensing Apparatus

Environment

The electrochemical sensor and sensing apparatus may be used to qualitatively or semi-quantitatively determine the amount of an analyte, for example a protein, present at the environment to which the sensor or apparatus is deployed.

The environment may be a biological sample, such as an extract, from a subject. For example, the sample may be a stool sample, or a sample of another body fluid such as lumen, digestive enzymes, or wound fluid. In one preferred embodiment, the sample is a stool sample. In another preferred embodiment, the sample is an intestinal fluid sample.

The electrochemical sensor may be used to determine whether the level of protein in a sample is at physiological level, that is the level expected in a healthy subject, or a clinical level, that is the level that is abnormal, or a level that is associated with a disease state.

In one embodiment, the clinical level may be associated with an excess of protein compared to the physiological level.

In one embodiment, the clinical level may be associated with an absence or reduced level of protein compared to the physiological level.

The sample may be analysed without modification after it is taken from the subject. Alternatively, the sample may be treated, for example to improve its properties as an electrolyte for the electrochemical sensor of the invention.

The sample may be diluted, with water, acid or buffer solution. The water, acid or buffer solution may be used to alter the pH and/or ionic strength of the sample.

Where the sample is a stool sample, the diluent is used to transform the sample into a state more suitable for electrochemical analysis. Thus, the diluent may act to solubilise portions of the stool. The diluent may act to extract components from the stool matrix, including, for example, blood. Where cell components are present in a sample, such as blood cells, the diluent may be added to lyse the cells and release the cell contents. Where a stool sample contains blood, those cells may be lysed in order to release Hb into solution. As noted above, the diluent may be added to provide appropriate pH and ionic strength control. Thus, the diluent may have the effect of acting as a buffered electrolyte for the later electrochemical analysis of the sample.

In a particularly preferred embodiment, the diluent is Buffer A comprising 0.1% saponin. 1.0×Buffer A is 100 mM citrate-phosphate, pH 5.0+100 mM KCl. Buffer A may be used at from 0.1× to 1.0× concentration as a diluent for a stool sample. The diluent may be used with additional components as described herein.

Dilution may provide a sample having a pH and ionic strength that is more suitable for analysis.

Preferably, a stool sample is diluted with at least 2×, at least 5×, at least 10×, or at least 20× by volume of the diluent. The stool sample may be diluted with at least 5 to 10× by volume of the diluent, and most preferably about 5× by volume of the diluent.

In a typical preparation, 200 mg of a collected stool sample is solubilised in 2 mL of diluent, such as a buffer.

Where the electrochemical sensor is used to detect Hb or another protein component of blood, the sample is preferably treated with a cell lysing agent. The lysing agent is suitable for lysing red blood cells (erythrocytes) in a sample to make available Hb for catalysis of the reaction between the first and second reagents. Preferably, the agent is not electrochemically active under the conditions used to analyse the sample.

The lysing agent may be selected from the group consisting of saponin, EDTA, sodium deoxycholate, surfynol and other related polyacetylenics, Triton X-100, Tween 20, sodium lauryl sulphate, and digitonin. Alternatively, or additionally, commercially available lysing products may be used. One example is the Red Blood Cell Lysing Buffer Hybri-Max available from Sigma-Aldrich (product number R7757, for example).

Preferably, the sample is treated with saponin. This agent has been found not to interfere with the electrochemical analysis of a biological sample, including a Hb-containing sample.

The sample may be at a temperature of around 37° C. Alternatively the sample may be at room temperature. For example, the sample may be at a temperature in the range 10 to 30° C., preferably 15 to 25° C. The temperature of the sample may be adjusted to bring it to the preferred temperature. For example, the sample may be cooled or allowed to cool from physiological temperature to room temperature.

In some embodiments, it is preferred that the sample is at about room temperature, at which temperature optimal sensor performance is obtained.

Preferably the sample is at a pH of 3 to 8, preferably 4 to 5, preferably about 5. The pH of the sample may be adjusted to bring it to the preferred pH. Preferably the pH of the sample is adjusted by a buffer or an acid held in the working electrode.

A wetting additive may be added to the sample to improve the wetting of the working electrode. The wetting additive is preferably used in combination with a buffer, which is provided to regulate the pH of an environment. The wetting additive may be selected from those wetting additives described above in relation to the optional electrode additives.

Preferably the sample is a sample from a subject on a diet control regime, such as those diets described below.

Preferably the sample is a sample from a subject on a diet control regime, wherein the diet is controlled such that food items in food categories 1-5 are not present in the diet, or consumption of those food items is limited, for at least 24 hours before the sample is taken from the subject.

Preferably the sample is a sample, such as an intestinal fluid sample, from a subject on a diet control regime, wherein the diet is controlled such that vitamin C, acetaminophen, salicylates, and uric acid and are not present in the diet, or consumption of those substances is limited, for at least 24 hours before the sample is taken from the subject.

Preferably the sample is a from a fasting subject, where the sample is taken from the subject at least 12 hours after the start of the fasting regime.

A sample may be a fluid in the gastrointestinal tract of a subject.

The environment to which the sensor or apparatus is deployed may be a region of the gastrointestinal tract of a subject. This region may be the upper or lower gastrointestinal tract, or both. The lower gastrointestinal tract may be the small intestine, which includes the duodenum, jejunum and ileum. The lower gastrointestinal tract may be the large intestine, which includes the cecum, the colon and rectum. The colon may be the ascending, transverse or descending part of the colon.

Protein

The electrochemical sensor of the invention may be used to detect a protein (which may be referred to as the analyte) at a particular environment.

The protein is capable of catalysing a reaction between the first reagent and the oxidising agent. The first reagent and the oxidising agent may be selected with a target protein (or analyte) in mind.

Preferably, the protein is a catalyst for the reaction of hydrogen peroxide with the first reagent.

The protein may be a metalloprotein. Preferably, the protein is horseradish peroxidase or haemoglobin. Most preferably the protein is haemoglobin. In this most preferred embodiment, the electrochemical sensor and sensing apparatus of the invention are suitable for use in the detection of blood at a particular environment.

The protein may itself be associated with an analyte of interest. The analyte may be a biomolecule, such as those biomolecules that are, or comprise, a polynucleic acid, a polypeptide, or a polysaccharide. The protein may be considered as a label for the analyte that allows the detection, and optionally quantification of the analyte, in a sample. Such detection and analysis is based on the catalytic activity of the protein label.

Typically, the protein is covalently bonded to the analyte, for example by disulfide, amide or ester bonds, as is known to a person of skill in the art. In other embodiments, the protein and the analyte may be linked by other, non-covalent interactions, such as hydrogen bonding.

In the presence of the protein, the first and second reagent react at a rate 100 times or more, 500 times or more, or 1,000 times or more than the reaction of the first and second reagent in the absence of the protein.

The rate of reaction of the first and second reagent in the presence and absence of the protein may be determined electrochemically.

Subject

The electrochemical sensor may be used to detect the presence of a protein in a sample from a subject. Alternatively the sensor may be used to detect the presence of a protein at a particular location on or in a subject.

The subject may be an animal, a mammal, a placental mammal, a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject may be in any of its forms of development, for example, a foetus.

In one preferred embodiment, the subject is a human.

Use and Methods

In one aspect of the invention, there is provided the use of an electrochemical sensor in the detection of a protein. The electrochemical sensor may find use in the detection of blood at an environment to which the sensor is deployed.

In a further aspect of the invention there is provided a method for detecting a protein, the method comprising the steps of:

(i) providing an electrochemical sensor, the electrochemical sensor comprising:
   a working electrode having an electrically conductive matrix holding a first reagent and/or a second reagent, the second reagent being an oxidising agent or a precursor thereof for the first reagent;
   a counter electrode and optionally a reference electrode;
   wherein a reaction between the first reagent and the oxidising agent is catalysable by the protein to provide a detectable signal at the working electrode;
   and the electrically conductive matrix is an electrically conductive carbon- or graphite-containing matrix or an electrically conductive porous matrix;
(ii) making available the electrochemical sensor at an environment to be analysed for the protein;
(iii) making available for reaction a first reagent and a second reagent;
(iv) maintaining a potential across the working electrode and the counter electrode and/or the reference electrode, where present; and
(v) measuring the current passing between the working electrode and the counter and/or reference electrode where present.

In one embodiment, the electrochemical sensor includes a working electrode comprising an electrically conductive matrix holding a first reagent and a second reagent.

In one embodiment, the electrochemical sensor includes a working electrode comprising an electrically conductive matrix holding one of a first reagent or a second reagent. The other of the first reagent or the second reagent is made available for reaction with one of the first reagent or the second reagent upon activation of the electrochemical sensor.

The other reagent may be present at the environment to which the sensor is deployed. For example the other reagent may be added to a sample taken from a subject. Alternatively, the other reagent may be contained in a reagent space of the electrochemical sensor. The reagent space is separated from the electrolyte space. The reagent space is exposable to said environment and the electrolyte space on activation of the electrochemical sensor.

The electrochemical sensor may be in an apparatus, preferably a pill, which is deployed at the environment to be analysed. The pill may be adapted to be swallowable, or implantable in the human or animal body, or it may be adapted to be placed at a surface location of the human or animal body.

The environment to be tested may be a biological sample taken from the human or animal body. Thus the electrochemical sensor is made available for analysis of that sample. The apparatus may be provided with a sample chamber which is exposed to an electrochemical sensor. A biological sample may be added to the sample chamber for analysis.

The first and the second reagent are made available for reaction. The reaction is catalysable by a protein to provide a detectable signal at the working electrode. Where only one of the reagents is a component of the working electrode, the other of the reagents is made available for contact with the working electrode. The other reagent is permitted to penetrate the matrix where it is made available to react with the one of the reagents in the presence of the protein.

Where both reagents are provided within the working electrode, they may be considered available for reaction. In the absence of a protein the rate of reaction between the first and second reagent is low, if not substantially non-existent.

Testing

Peroxidase levels at the environment to which the sensor or apparatus is made available may affect the readings obtained, and may generate false positives. Increased levels of peroxidase activity in blood are associated with certain foodstuffs within a subject's diet. Such increases are particularly pronounced in a diet including raw fruits and vegetables.

The device and apparatus of the invention may be used to test for the presence of blood in a subject on a peroxidase-controlled, specifically a peroxidase-reduced, diet. The subject may be tested 24 hours or more, or 48 hours or more into the peroxidase-controlled diet.

The diet may be controlled such that food items responsible for a high level of peroxidase activity in blood, for example food stuffs in groups 1-5 above, are removed or limited in the diet. Alternatively, the subject may be placed on a fasting regime for at least 12 hours, at least 24 hours or at least 36 hours prior to testing.

Table 1 shows the levels of peroxidase activity associated with a range of common foodstuffs (adapted from Caligiore et al. *Am. J. Clin. Nutr.* 1982, 35, 1487).

TABLE 1

The peroxidase levels in certain food items grouped according to the mass of food with peroxidase activity equivalent of 1.0 mL of blood. All food items are raw, unless stated.

| Category | Mass of food with peroxidase activity equivalent of 1.0 mL of blood g | Food items |
|---|---|---|
| 1 | <5 | Broccoli, turnip |
| 2 | 5-10 | Rare red meat, cantaloupe, red radish, parsnip |
| 3 | 10-20 | Jerusalem artichoke, bean-shoots, cucumber, French beans, lemon rind, mushroom, parsley, courgette |
| 4 | 20-50 | Grapefruit, carrot, cabbage, potato, pumpkin, fig |
| 5 | 50-100 | Peach celery, lettuce, pepper (pickled) spinach |
| 6 | 100-500 | Blackberries, pineapple, watermelon, walnuts, mint, peppers |
| 7 | 500-1,000 | Banana, black grapes, pear, plum |
| 8 | >1,000 | Well-cooked red meat, apples, apricots, olives, raspberries |
| 9 | Undetectable | Roast chicken and turkey; boiled fish; boiled liver, kidney and brains; boiled pork, ham and bacon; boiled silverside, dates, white grapes, lemon, nectarine, orange, passion fruit, raisins, strawberries, sultanas, tomato |

DETAILED DESCRIPTION OF AN EMBODIMENT OF THE INVENTION

An embodiment of the sensing device of the invention will now be described with reference to FIGS. 1 and 2.

The sensing device of the invention comprises one working electrode, and optionally a second working electrode, which may be the same or different to the first working electrode, a counter electrode and optionally a reference electrode.

Figure 1:
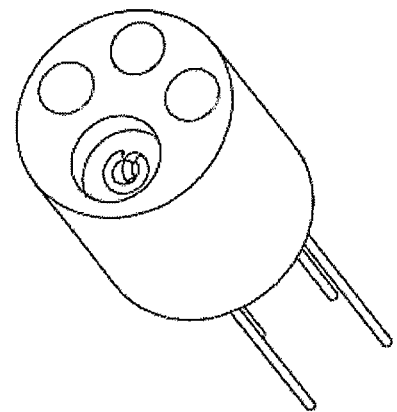
FIG. 1 is a perspective view of an embodiment of a sensing device of the invention, the sensing device having two working electrodes for operation in a differential or duplicate mode, a counter electrode, and a reference electrode all held within an electrode cap.
Figure 2:
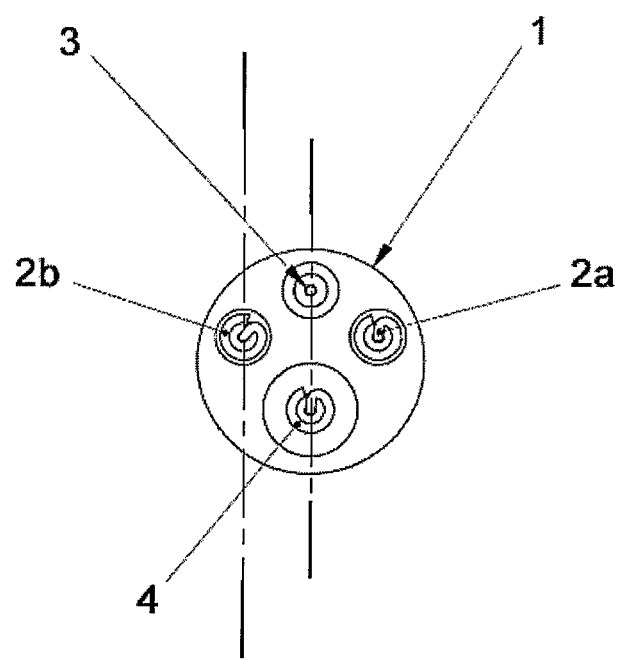
FIG. 2 is a plan view of the contact end of the electrode cap of the sensing device of FIG. 1. The working electrodes are shown as empty cavities with electrical contacts at the bottom.

FIG. 1 is a perspective view of a sensing device having two working electrodes (marked grey in the figure) held within separate cavities in an electrode cap. FIG. 2 is a plan view of the end of the electrode cap 1 that is intended for exposure to a sample solution. The working electrodes 2a and 2b are spaced apart in the electrode cap in separate cavities. The working electrode matrix fills the cavity, and the surface of each working electrode is flush with the cavity surface.

The electrode cap 1 holds a counter electrode 4 within a further cavity. The counter electrode 4 is a coiled wire for increased surface contact with the sample solution. The wire may be steel or platinum, although steel is preferred on the basis of cost.

The electrode cap 1 also holds a reference electrode 3 in an additional cavity.

Each of the electrodes is adapted for connection to a power supply. Each electrode in the cap is provided with a contact wire for connection to a power source. These contact wires extend out of the cap at the end opposite to that end that is intended for exposure to the sample solution.

The cap may be placed in a sample solution such that each of the electrodes contact the sample solution.

The cap itself may be constructed from an inert plastics material. The material may be suitably molded to allow it to hold a series of electrodes. Alternatively, the cap may be machined in order to provide most suitable cavities. The cap is not particularly limited in size or shape. However, the present inventors have found that a substantially cylindrical cap is especially useful as it may be readily inserted into vials and other such reservoirs. In one working embodiment, the cap has a diameter of about 6 mm, which permits the cap to be inserted into standard 2 mL sample reservoirs.

The cavities are not particularly limited in size or shape (although the maximum size of the cavity is limited by the size of the cap itself). For practical reasons it may be beneficial to have substantially cylindrical cavities. For a 6 mm diameter cap, the inventors have found that cavities having a diameter of about 1.5 to 2.0 mm are suitable. The cavity need only be as deep as is required to hold the electrode. The cavity is sufficiently deep as to hold the electrode flush with the cap surface.

Modifications of these embodiments, further embodiments and modifications thereof will be apparent to the skilled person on reading this disclosure, and as such these are within the scope of the present invention.

Examples

The following examples are provided solely for illustrative purposes and are not intended to limit the scope of the invention, as described herein.

Carbon Paste Electrode with TMB and URP or Sodium Perborate

Working Electrode Preparation

An electrode having TMB and URP in a carbon paste matrix was prepared. URP and TMB were separately ground to finer powders using a mortar and pestle. The required amounts of finely ground TMB and URP were then weighted into a 2 mL microcentrifuge tube, which was vortexed at full speed for a few seconds. The required amount of carbon paste was then added to the mix, and the tube vortexed again. The blend was then thoroughly homogenised using a round-ended glass rod.

A small amount of the blend was packed into a cut-off pipette tip. A second cut-off pipette tip comprising a metallic wire was then inserted into the first tip, and the wire was brought into contact with the plug of blend. This wire was used to connect the electrode to the control electronics. The resulting plug of blend within the first pipette tip was about 0.3 mm in diameter and about 1 mm thick.

TMB was used at around 5 wt % with respect to the carbon paste.

URP was used at around 7 wt % with respect to the carbon paste.

An electrode having TMB and sodium perborate in a carbon paste matrix was prepared in a similar manner to the TMB and URP electrode described above. The TMB was used at around 5 wt % with respect to the carbon paste. Sodium perborate was used at around 7 wt % with respect to the carbon paste.

Sensing Device

A sensing device comprising the electrode described above was set up. The device comprised one or more of the working electrodes described above, a counter electrode of coiled Pt wire, and a commercial Ag/AgCl (sat) electrode (available from BAS Inc). The electrodes were electrically connected through a purpose-built printed circuit board (PCB) capable of providing a constant potential bias between the working and reference electrodes. The PCB was connected to a power supply and a digital voltmeter (both from Agilent) interfaced with a computer.

Sensing Apparatus

A sensing apparatus comprising the sensing device described above was prepared. The apparatus comprised the sensing device, which was placed in a 5 mL beaker containing about 2 mL of a sample solution. A thermostat-controlled water bath and jacketed vessel were used for temperature control.

Sensing Operation

A typical protocol for the operation of the sensing apparatus included the steps of:
 introducing a sample into the beaker;
 immersing at least the electrodes of the sensing device in the sample;
 applying a potential bias across the electrodes a few seconds after the immersion;
 and recording the electrochemical response, typically for a few minutes.

Sensor Testing

The sample used for testing typically comprised 0.1× Buffer A (1.0×Buffer A is 100 mM citrate-phosphate, pH 5.0+100 mM KCl). The sample temperature was typically about 37° C. Initial experiments using cyclic voltammetry has shown that optimum sensor performance is obtained for a potential bias of +0.10 V (versus an Ag/AgCl (sat) reference electrode), in pH 5 buffer.

Lyophilised human haemoglobin (Sigma) was dissolved to 10-40 mg/mL in 10 mM potassium phosphate buffer (KPi) pH 7.4. This stock solution (prepared fresh daily) was diluted in testing medium (max 100 µL of Hb stock solution in 2 mL electrolyte).

As an example, a sample comprising Hb at a concentration of 2 mg/mL in 0.1 Buffer A at pH 5.0 was analysed using a dual electrode sensing apparatus having two 0.3 mm carbon paste electrodes comprising 5 wt % TMB and 7 wt % URP.

Figure 3:
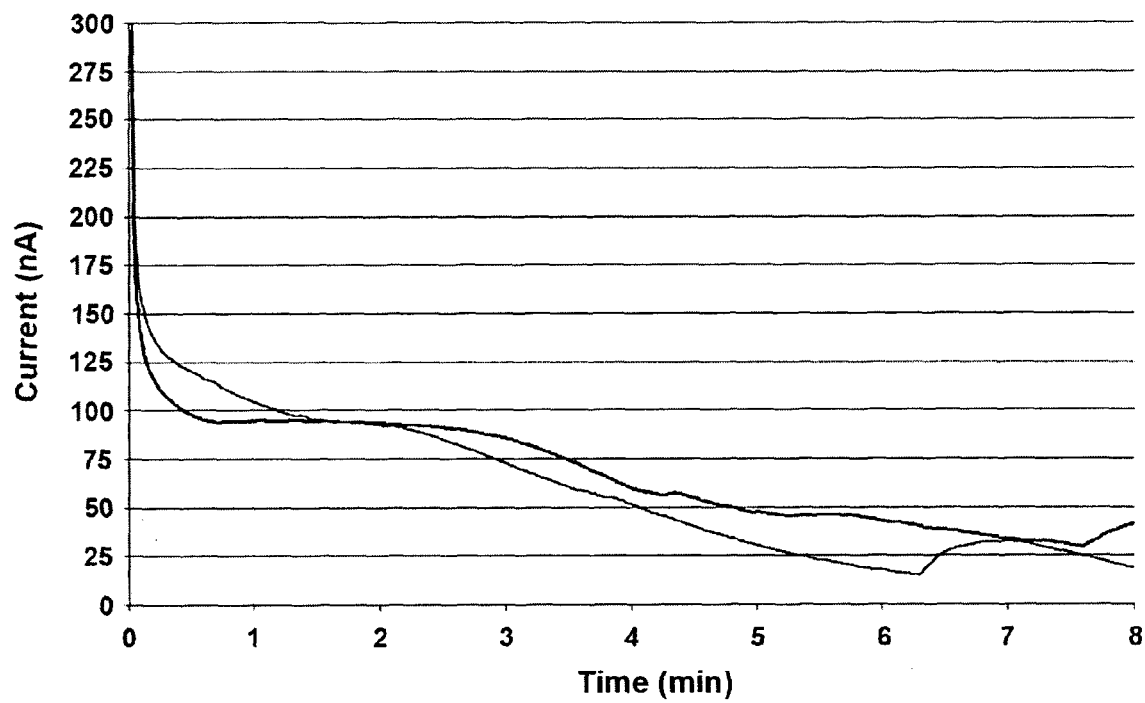
FIG. 3 shows the response curves recorded at two TMB- and URP-containing carbon paste working electrodes used to electrochemically analyse a sample comprising Hb (at a concentration of 2 mg/mL) in 0.1×Buffer A.

The response curve, showing the current measured at the working electrode as a function of time, is shown in FIG. 3. The response curve starts with a current "spike" which represents charging current. This subsides within the first minute. From this point on the majority of the recorded signal corresponded to electrochemical reduction of the oxidised form of TMB.

The mean current intensity taken as an average of the signal recorded continuously between two time points, $T_1$ and $T_2$, may be used to determine, qualitatively, the concentration of haemoglobin present in a sample. Signal recording begins (at time $T_1$) after the charging current spike has subsided, typically 15 seconds after a voltage is first applied across the electrodes. Signal recording ends (at time $T_2$) after about 120 seconds.

Figure 4:
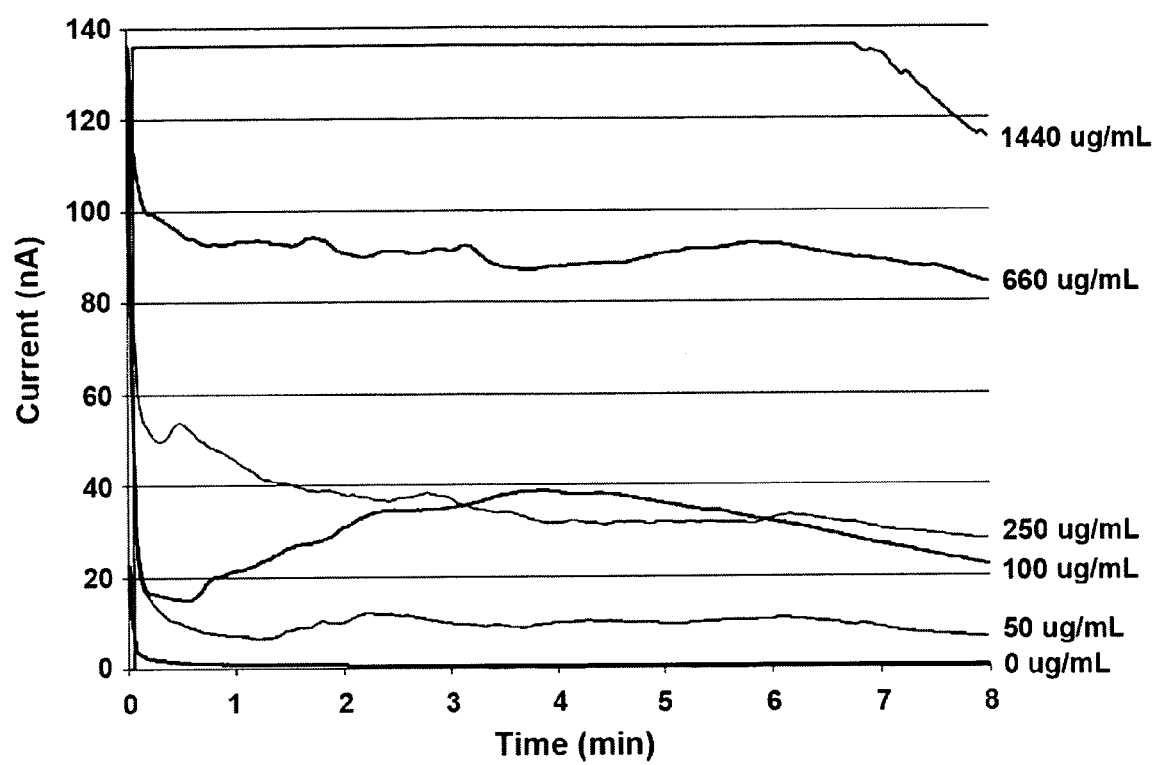
FIG. 4 shows the response curves recorded at a TMB- and URP-containing carbon paste working electrode used to electrochemically analyse a series of samples of increasing Hb concentration. The samples were 0.1×Buffer A solutions at pH 5.0 to which increasing amounts of Hb in buffer was added. The upper curves correspond to those responses recorded for samples having a higher Hb concentration. Each curve is the average of three independent runs.

The sensing apparatus was tested against a series of samples of increasing Hb concentration from 0 to 1.44 mg/mL. FIG. 4 shows the response curves for each of the samples. Each curve is the average of three independent runs.

The curve for the 1.44 mg/mL Hb sample shows saturation of the controlled electronics (operational amplifier). This was subsequently remedied by adjusting the input resistor.

Figure 5:
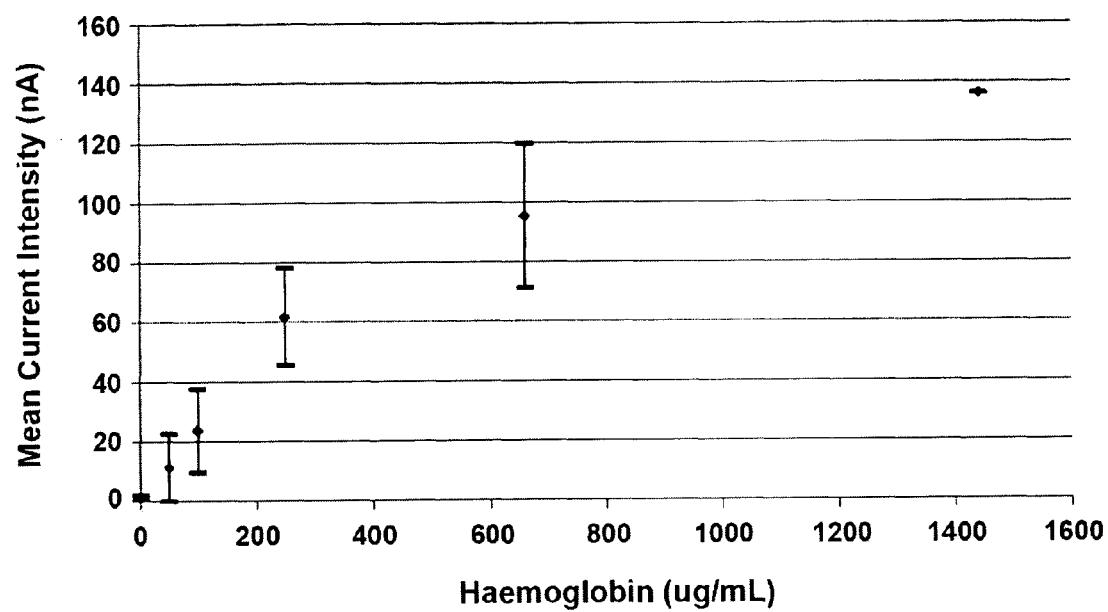
FIG. 5 is a graph showing the mean current intensity calculated from each of the response curves of FIG. 4 with respect to the known Hb concentration in each sample. Each data point represents the average of three independent measurements. The error bars correspond to the standard deviation over the three independent measurements.

Using the mean current intensity values calculated from each of the response curves, a "calibration curve" was prepared showing the semi-quantitative capacity of the sensor to detect haemoglobin concentration (see FIG. 5). The information in FIG. 5 is based on the average of the current recorded at 15 second ($T_1$) and 135 seconds ($T_2$).

The calibration curves show that samples containing different amounts of Hb can be qualitatively distinguished on the basis of their mean current intensities.

Analysis of a Blood Sample

The sensor was tested against a range of blood samples of increasing Hb concentration. Blood was sampled from a healthy donor and lysed in 0.1×Buffer A (9:1, Buffer A: blood). Blood was tested at following dilutions (in 0.1×Buffer A): 100×, 200×, 400×, and 800×. This corresponded to Hb concentrations of 1,500 to 187.5 μg/mL (assuming a concentration of Hb at 150 mg/mL in blood). A blank sample (no blood) was also measured. A "calibration curve" was prepared as before, and the relationship between the mean current intensity values and the Hb concentration in a particular sample is shown in FIG. 6.

Figure 6:
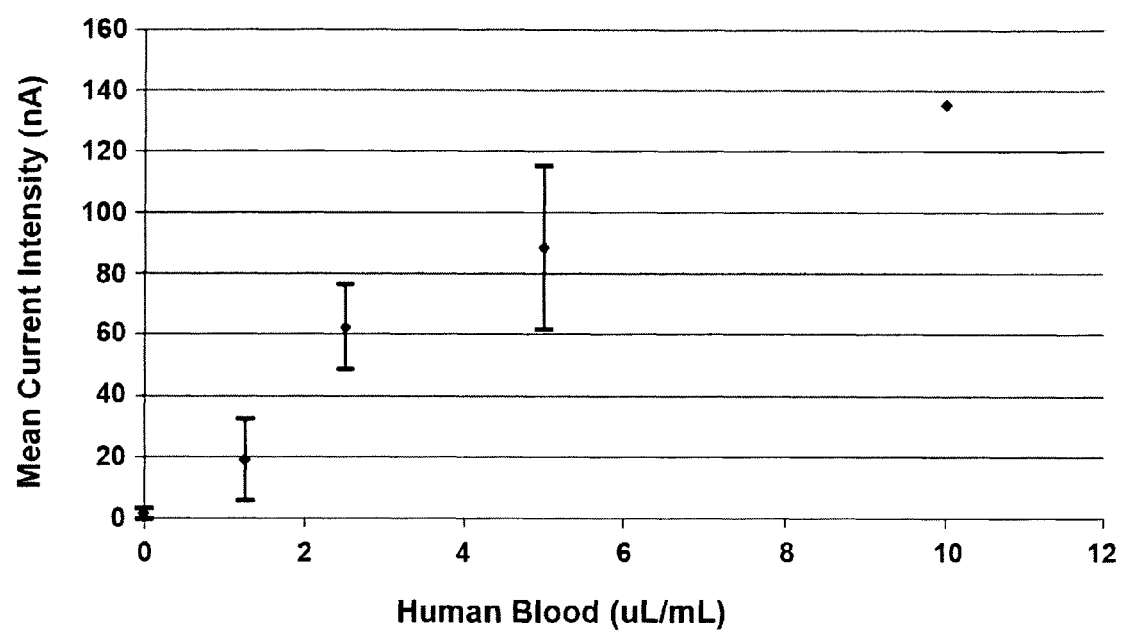
FIG. 6 is a graph showing the mean current intensity calculated from response curves recorded at a TMB- and URP-containing carbon paste working electrode used to electrochemically analyse a series of samples of decreasing blood concentration. The samples were derived from blood lysed with 0.1×Buffer A solutions at pH 5.0, which were serially diluted to give a series of samples of decreasing blood concentration. Each data point represents the average of three independent measurements. The error bars correspond to the standard deviation over the three independent measurements.

FIG. 6 shows that the mean current intensity for samples having 1.2 μL/mL of human blood in buffer (which corresponds to the level of Hb present at a physiological level) and for samples having 2.5 μL/mL of human blood in buffer (which corresponds to the level of Hb present at a clinical level) are clearly distinguishable.

Figure 7:
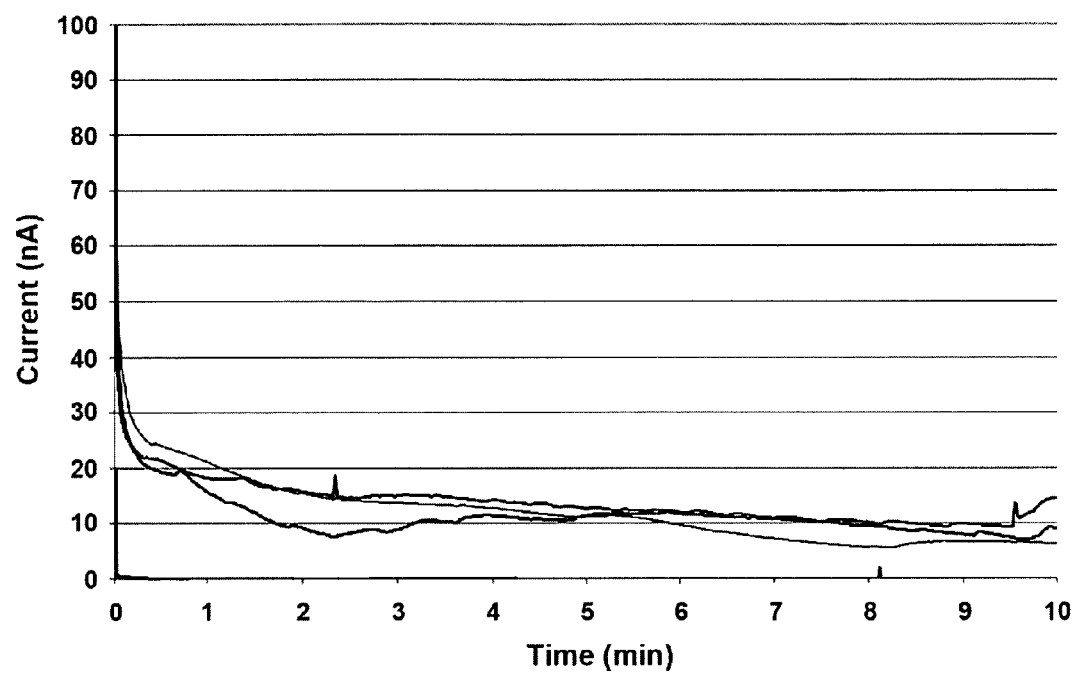
FIG. 7 shows the response curves recorded at a TMB- and URP-containing carbon paste working electrode used to electrochemically analyse a series of Hb-containing stool samples. The samples were 0.1×Buffer C solutions at pH 7.4 to which Hb was added. The upper three curves correspond to those responses recorded for samples where Hb was present. The lower curve corresponds to the control sample having no Hb present.

The pH in the small and large bowel is in the range 6.0-7.5. Hence, to work in this environment, the sensor is required to function within this pH range. Performance of the sensor was tested at pH 7.4. The buffer used was 0.1×Buffer C. (1.0× Buffer C: 100 mM citrate-phosphate buffer, pH 7.4+100 mM KCl). The response curves for three independent haemoglobin samples are shown in FIG. 7 along with the control curves for the blank (buffer only) samples. Whilst the response curves show a reduction in signal levels as compared to the samples at pH 5.0, Hb can still be detected at a concentration 2 mg/mL.

The performance of the sensor in pH 7.4 media was found to improve when used with a built-in pH control, as described below.

Analysis of a Stool Sample

Illeal effluent was used as a model for the GI tract environment (intestinal "juice" encountered in vivo). Illeal effluent was obtained from ileostomy patients. The patients were not on a controlled diet regime prior to the ileostomy, and a range of foods stuffs featured in the diet. As a consequence, the samples were considered a suitable representation of the types of sample that could and would be encountered in a real environment.

Model stool (as encountered in the colon) was prepared by condensing illeal effluent in a centrifuge. Illeal effluent samples obtained from a local hospital were pooled, aliquoted (10 mL) and stored at −20° C. Model stool was made as follows: an aliquot was thawed, then centrifuged at 4,000 rpm for 5 min; the supernatant was discarded using a 1 mL Gilson pipette, taking care not to disturb the sediment; and the semi-solid fraction was scooped out of the tube using a spatula. The amount of condensed material obtained from one aliquot was about 3 mL or 3.1-3.2 g.

Fresh whole human blood was collected from a healthy donor and used on the same day.

Positive samples were prepared by spiking model stool with blood, in known amounts, and mixing with a glass rod.

The data shown was generated from model stool obtained by pooling several batches of illeal effluent. This had a pH of 7.4.

Figure 8:
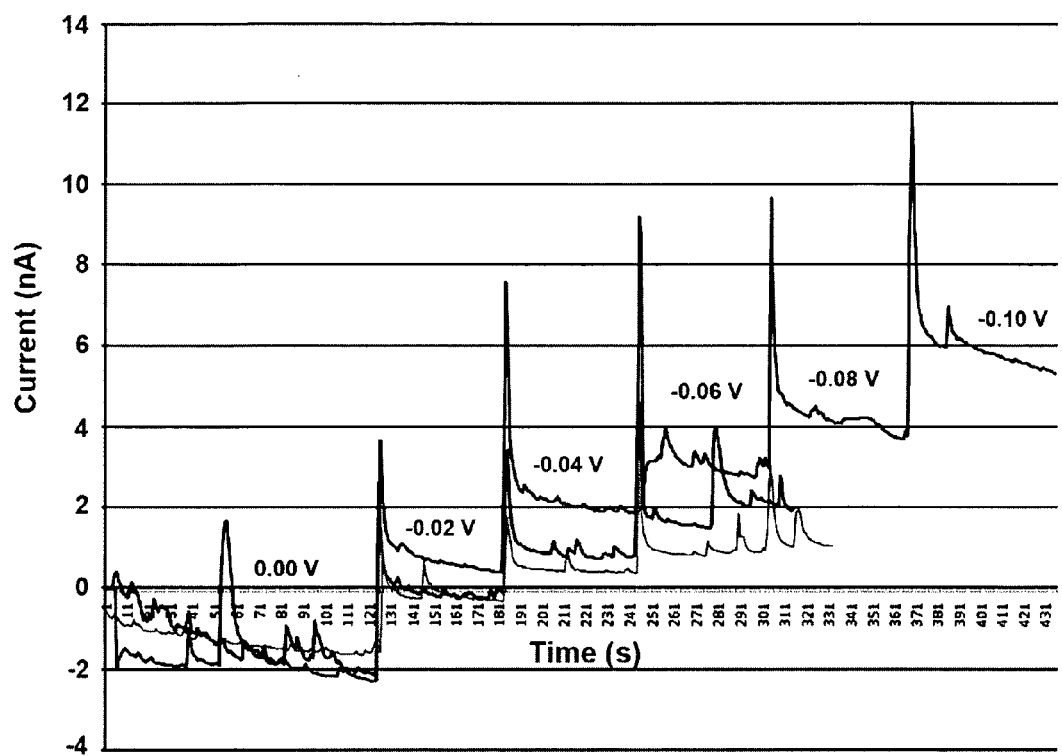
FIG. 8 shows the response curves recorded over three separate runs for a blank condensed illeal effluent sample having no Hb present. The curves were recorded across the range of potentials from 0.00 to −0.10 V.

On testing the sensor (which comprised a carbon paste electrode with TMB and URP) in this environment it was found that values of potential bias previously used in citrate-phosphate buffer gave significantly non-zero baseline current levels. The potential bias had to be adjusted to a value of −0.02 V for the blank (no Hb present) current levels to be within +/−1 nA, as shown in the chronoamperometry curve in FIG. 8.

Figure 9:
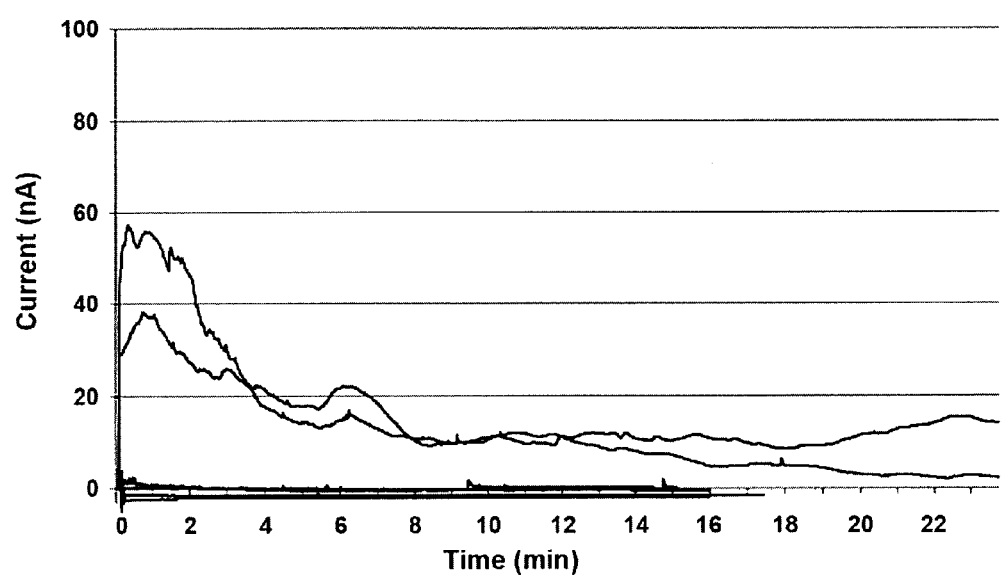
FIG. 9 shows the response curves recorded at TMB- and URP-containing carbon paste working electrodes used to electrochemically analyse a series of stool samples (condensed illeal effluent) containing Hb. The upper curves correspond to a sample where Hb was present at 3.6 mg/mL.

When the system was operated at this potential bias the sensor was able to detect Hb at a level of 3.6 mg/mL in condensed illeal effluent, as shown in FIG. 9.

Further experiments were conducted on model stool samples using a sensor having a carbon paste electrode with TMB and sodium perborate. The stool samples were prepared as described above using condensed illeal effluent to which varying amounts of fresh whole human blood was added. The test samples were prepared by adding 0.4, 1.0 and 2.0 wt % of blood to illeal effluent prior to dilution with buffer. A reference sample having no blood was also tested.

After the effluent and blood were mixed, a 0.4 g sample was diluted with 2 mL of 1×Buffer A further comprising 0.1% saponin. The resulting mixture was shaken to solubilise the stool prior to analysis.

For reference, samples having 0.4 wt % of blood to illeal effluent were tested against three separate electrodes. The carbon paste electrodes were prepared the day before the measurements were taken, and were prepared from the same batch of materials.

The current recorded at the electrodes over time after exposure of the electrodes to the diluted stool sample is shown in FIG. 15.

Three further TMB- and sodium perborate-containing carbon paste electrodes were prepared and each electrode was used in an electrochemical sensor to evaluate the percentage blood present in further simulated stool samples.

The stool samples were prepared as described previously. The simulated stool samples were prepared having no blood present, and 0.25 wt %, 0.5 wt %, 1 wt %, 2 wt % and 4 wt % added blood. Thus, for each sample 2.0 g of condensed illeal effluent containing a known amount of blood was diluted with 10 mL of 1×Buffer A with 0.1% saponin. The diluted sample was then split into five 2 mL fractions, and each fraction was subjected to electrochemical analysis with a carbon paste electrode.

The response curves recorded for each of the samples were used to establish mean current intensities. FIG. 16 is a graph showing the mean current intensity for each of the series of test samples. Each data point represents the average of five independent measurements (three different electrodes). The error bars correspond to the 95% confidence interval over the five independent measurements.

The electrodes used in these experiments were prepared two days prior to their use, and were prepared from the same batch of materials.

Stability

Shelf life studies were carried out at room temperature. No significant loss of performance was observed over a period of 30 days.

In a specific example, a series of three paste electrodes comprising TMB and sodium perborate were prepared and stored for a period of three months after preparation. The performance of the electrodes at 1 week, 1 month and 3 months after preparation was measured. Thus, the net signal level (electrical current) for an electrode at each time was determined with respect to a standard analytical sample comprising 0.3 mg/mL Hb in 1×Buffer A (100 mM citrate-phosphate, pH 5.0+100 mM KCl). The electrodes were stored under a nitrogen atmosphere at room temperature.

The net signal level was set at 100 for the signals recorded 1 week after electrode preparation. The net signal level was seen to drop only slightly over the 3 month test period. Thus, after 1 month the net signal level was around 90% of the level recorded 1 week after electrode preparation, and after 3 months the net signal level was around 75% of the level recorded 1 week after electrode preparation.

The results of the tests are shown in FIG. 16. Each data point represents the average of three independent measurements from three different electrodes. All the electrodes were prepared from the same batch of materials. The error bars shown in the figure correspond to the standard deviation over the three independent measurements.

For applications in colon cancer diagnostics a capsule (and hence the sensor) will de facto be maintained at body temperature (around 37° C.) for the duration of its journey through the oesophagus, stomach, small intestine, large intestine and rectum. Experimentally determined retention times for an ingestible capsule travelling through the GI tract under the effect of peristalsis can be found in the literature (e.g. from scientific publications available from the SmartPill Inc. website—www.smartpillcorp.com): 3-7 hours for the capsule to reach the upper colon, and 27-48 hours to reach the rectum.

Sensor stability was tested over a period of 48 hours at 37° C.

Figure 10:
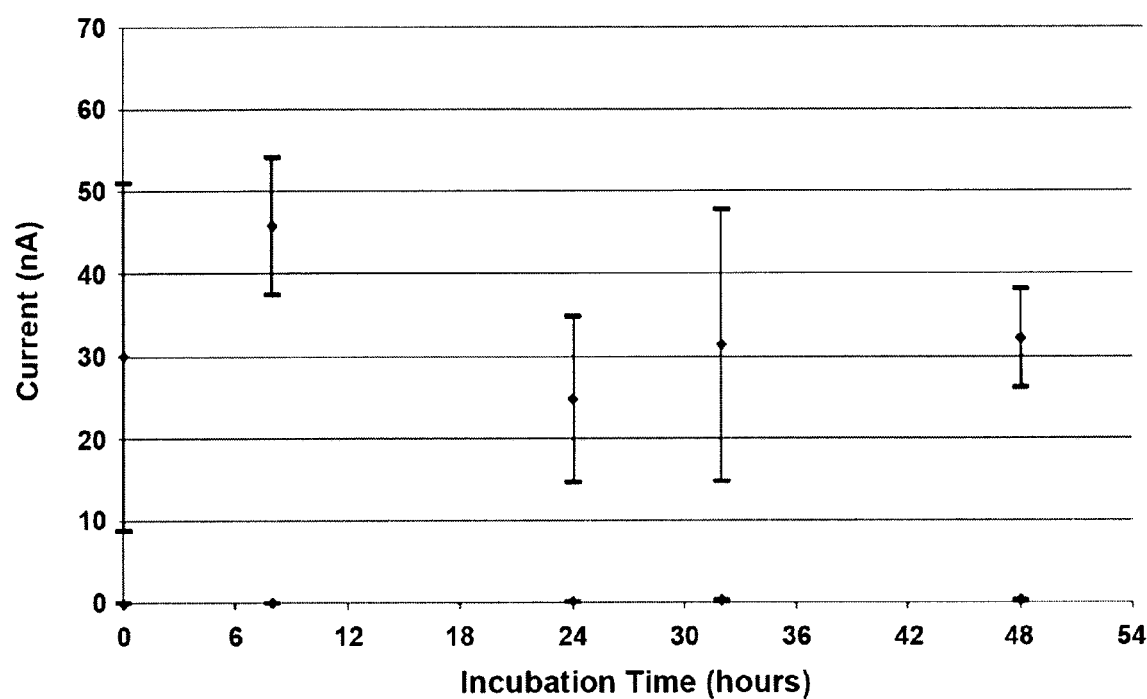
FIG. 10 is a graph showing the mean current intensity calculated from response curves recorded at a TMB- and URP-containing carbon paste working electrode used to electrochemically analyse samples containing Hb. The response curves were obtained after incubation of the working electrode for set periods of time. The lower mean current intensity values correspond to measurement taken against a sample having no Hb present.

FIG. 10 shows that the ability of the sensor to detect small amounts (250 μg/mL) of Hb is retained after 48 hours incubation at 37° C.

Electrode Additives

Mannitol Additive

The addition of a hygroscopic, water-soluble compound to the electrode blend was believed to offer superior sensor performance particularly with regard to sensitivity and response time. Accordingly, a carbon paste electrode comprising TMB (9 wt %), URP (7 wt %) and mannitol (40 wt %) was prepared.

The mannitol-containing blend was prepared in a similar manner to the carbon paste electrode with TMB and URP described above. TMB, URP and mannitol were individually ground with a pestle and mortar prior to incorporation into the blend. To the TMB was added mannitol, then URP, then carbon paste. After addition of each reagent the blend was homogenised by vortexing. After addition of the final reagent (carbon paste) the blend was homogenised in a mortar then vortexed, and the process was repeated until a uniform paste was obtained.

Figure 11:
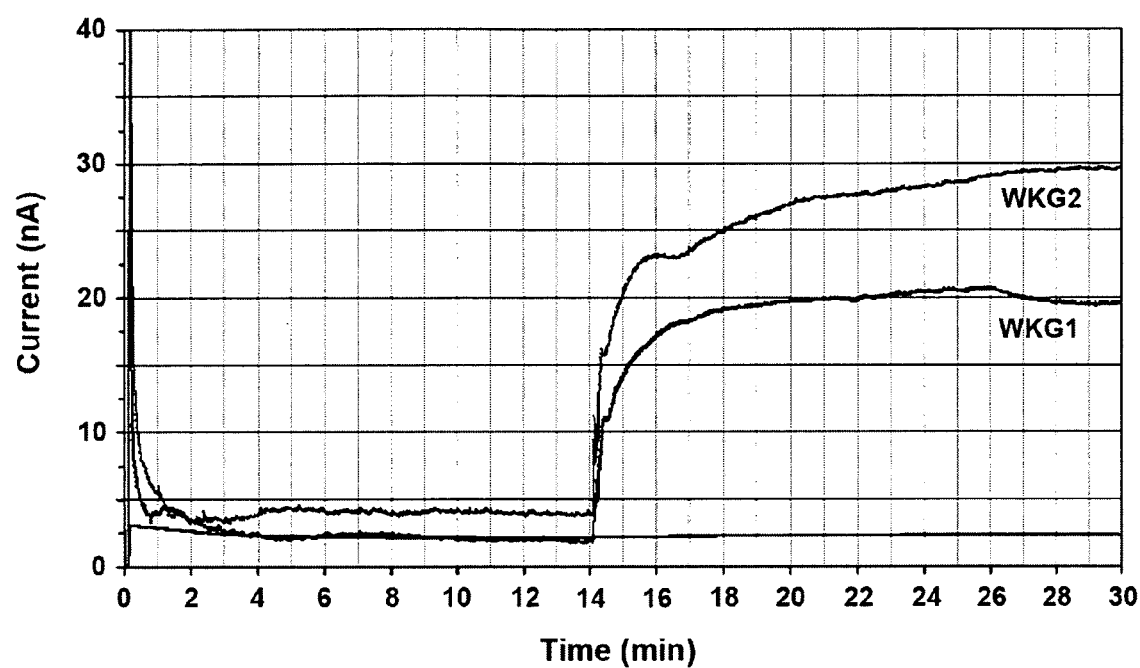
FIG. 11 shows the response curves recorded at a TMB- and URP-containing carbon paste working electrode used to electrochemically analyse a sample comprising Hb in 0.1×Buffer A. The upper curve (labelled WKG2) corresponds to the data recorded from a working electrode additionally comprising mannitol. The lower curve (labelled WKG1) corresponds to the data recorded from a working electrode that did not comprise mannitol.

FIG. 11 shows the response curves for the mannitol-containing electrode (upper line, WKG 2) compared with the basic electrode described above (lower line, WKG 1). The results were obtained in a single experiment.

The addition of a hygroscopic, water-soluble compound, such as mannitol, to the carbon paste blend is believed to improve the wettability of the electrode, and promotes the formation of a porous electrode structure, thereby providing an increased effective surface area and easier access of the analyte (such as Hb) to the bulk of the blend.

Without wishing to be bound by theory, it is believed that polyol compounds such as mannitol have a pH-lowering effect. As the optimal functional pH for the sensor is around pH 5, this pH-lowering effect could assist measurements taken on samples or in environments where the pH is higher.

pH Controlling Additive

The addition of a pH controlling agent to the electrode blend was investigated. As shown above, the optimal performance of the sensor is at a pH of around pH 5. However, the samples tested, or the environment into which the sensor is placed (such as sections of the GI tract) typically are of a pH in the range 6.0-7.5.

An electrode having a pH controlling agent, in this case a buffer, was prepared. A citrate buffer (citric acid+sodium citrate) and citric acid were used as buffering or pH-lowering agents. The electrode blend comprised carbon paste (50 wt %), MAN (38 wt %), TMB (1 wt %), sodium perborate (4 wt %), and citric acid (7 wt %). In some experiments sodium perborate tetrahydrate may be used in place of URP.

The electrode blend was prepared as described above. Thus, the reagents were added sequentially with vortexing after each addition. The citric acid was added as the final reagent before the addition of the carbon paste. Each of the reagents was ground with a pestle and mortar prior to incorporation into the blend.

The sensor was used with two working electrodes, each having the blend described above. The sensor was first activated in a "clean" buffer and the baseline current recorded for 14 minutes. A sample of Hb was then added in one portion into the solution (and mixed with a pipette). The final Hb concentration was 250 μg/mL. The buffer used was 0.1× Buffer C, pH 7.4.

Figure 12:
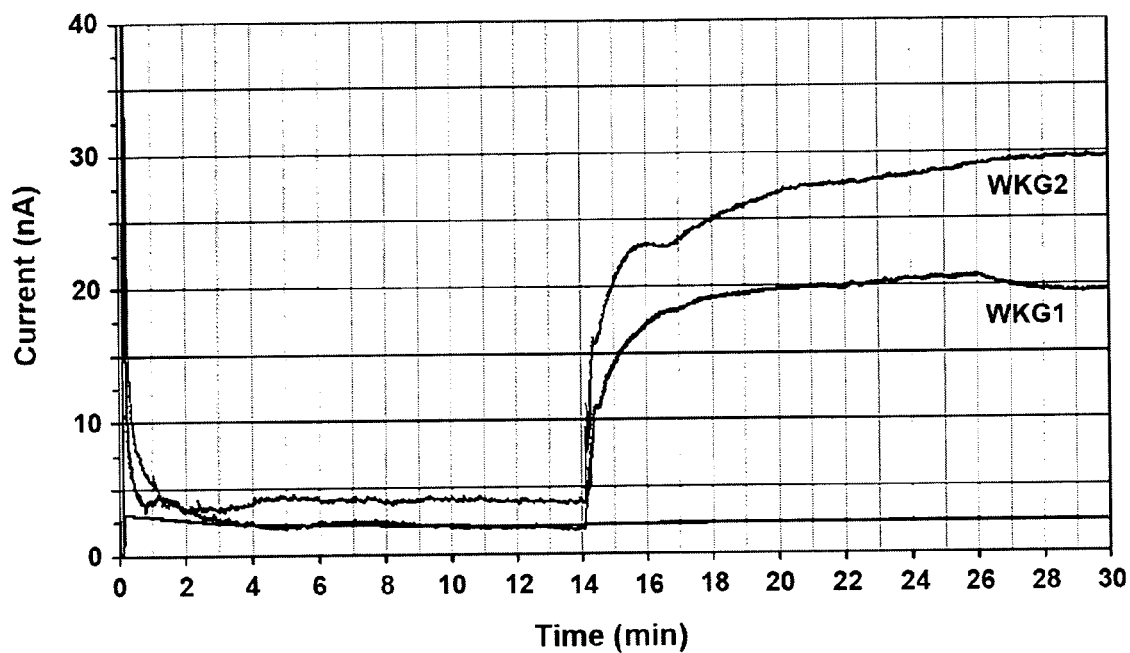
FIG. 12 shows the response curves recorded at a TMB-, URP-, and citric acid-containing carbon paste working electrodes used to electrochemically analyse a sample comprising 0.1×Buffer C at pH 7.4 to which Hb was added at 14 minutes.

FIG. 12 shows the response curves for each of the two citrate buffer-containing electrodes against the reference base line voltage recorded against the reference electrode. A marked increase in the recorded current was observed upon addition of the Hb sample, indicating that Hb can be detected using this electrode system at a concentration of 250 μg/mL.

The difference between the response curves for the two working electrodes can be partly ascribed to the non-uniformity of Hb distribution in the electrochemical cell after addition as a result of (insufficient) mixing. Batch variability as a result of blending inhomogeneity may also be responsible for signal differences between electrodes of the same composition. Automated blending may improve the homogeneity of electrode samples.

Figure 13A:
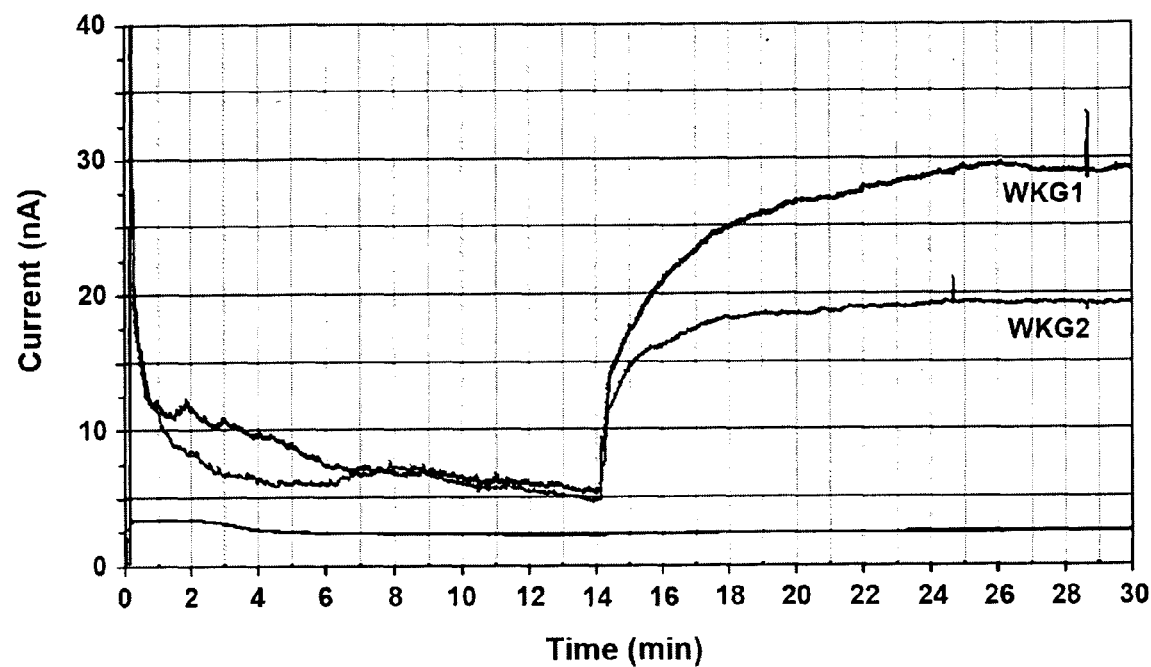
FIG. 13a shows the response curves recorded at a pair of TMB-, URP-, mannitol- and citric acid-containing carbon paste working electrodes used to electrochemically analyse a sample comprising 0.1×Buffer C at pH 7.4 to which Hb was added at 14 minutes. The electrodes had been incubated at 37° C. (in a dry state) for 20 hours prior to the analysis.
Figure 13B:
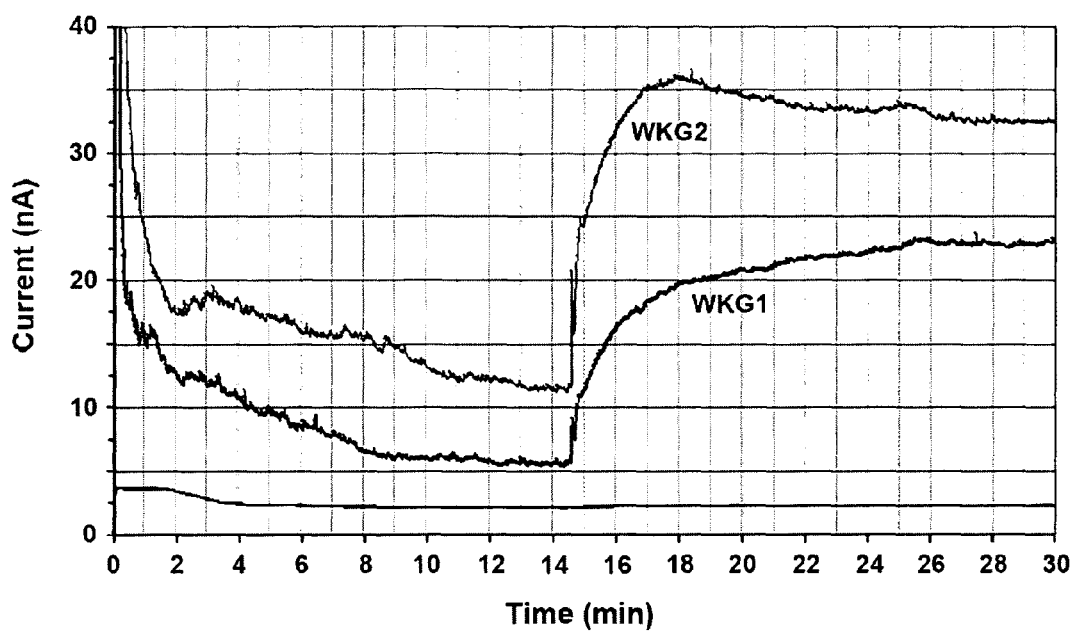
FIG. 13b shows the response curves recorded at a pair of TMB-, URP-, mannitol and citric acid-containing carbon paste working electrodes used to electrochemically analyse a sample comprising 0.1×Buffer C at pH 7.4 to which Hb was added at 14 minutes. The electrodes had been incubated at 37° C. (in a dry state) for 43 hours prior to the analysis.

The stability of the citric acid- and mannitol-containing electrode was tested by incubating the electrodes in buffer for 20 hours and 43 hours at around 37° C. The sensors were then used as before to detect the addition of a Hb sample to a buffer solution (0.1×Buffer C, pH 7.4.). FIG. 13a shows the response curves for the two working electrodes after 20 hours incubation, and FIG. 13b shows the response curves for the two working electrodes after 43 hours incubation.

Even after incubation at body temperature for 1-2 days the electrodes still exhibited sensitivity to 250 ug/mL Hb, in spite of a marked elevation in baseline (current level prior to injection of Hb) over time. Whilst the Hb concentration tested here is relatively low compared to realistic physiological levels; sensor performance can be considered acceptable.

Carbon Paste Electrode Comprising TMB or URP

Electrode Preparation

An electrode comprising TMB (9 wt %) in a carbon paste matrix was prepared in a similar manner to the electrode with TMB and URP.

Sensing Device and Sensing Apparatus

A sensing device and apparatus having a carbon paste and TMB electrode was set up in a similar manner to the electrode with TMB and URP describe above. The sample solution held in the beaker typically comprised 0.1×Buffer A at pH 5 with 2.7 mM URP.

Sensor Testing

The sensor comprising the carbon paste and TMB electrode was tested against a set of samples in the presence and absence of Hb. The response curves are shown in FIG. 14. The upper curves correspond to the responses recorded on samples comprising Hb at a concentration of 0.25 µg/mL in 0.1×Buffer A at pH 5 with 2.7 mM URP. The lower curve corresponds to the response recorded on a sample of 0.1× Buffer A at pH 5 with 2.7 mM URP with no Hb present. The results show that a carbon paste and TMB electrode may be used to detect the presence of Hb in a sample to which a second reagent, such as the oxidant URP, has been added.

REFERENCES

The following citations are hereby incorporated by reference in their entirety:

WO 2006/085087

Caligiore et al. *Am. J. Clin. Nutr.* 1982, 35, 1487

Petit, Gonzalez-Cortes and Kauffmann *Talanta* 1995, 42, 1783-1789. Preparation and characterization of a new enzyme electrode based on solid paraffin and activated graphite particles.

Sigma-Aldrich catalogue 2007/8

The invention claimed is:

1. A method for detecting a protein, the method comprising the steps of:
    (i) providing an electrochemical sensor, the electrochemical sensor comprising:
        a working electrode comprising an electrically conductive matrix holding a first reagent and/or a second reagent, the second reagent being an oxidising agent or a precursor thereof for the first reagent;
        a counter electrode and optionally a reference electrode;
        wherein a reaction between the first reagent and the oxidising agent is catalysable by the protein to provide a detectable signal at the working electrode; and
        the electrically conductive matrix is an electrically conductive carbon- or graphite containing matrix or an electrically conductive porous matrix;
    (ii) making available the electrochemical sensor at an environment to be analysed for the protein;
    (iii) making available for reaction the first reagent and the second reagent;
    (iv) maintaining a potential across the working electrode and the counter electrode and/or the reference electrode, where present; and
    (v) measuring the current passing between the working electrode and the counter and/or reference electrode where present.

2. The method according to claim 1, wherein the electrically conductive matrix is an electrically conductive carbon- or graphite-containing matrix.

3. The method according to claim 2, wherein the electrically conductive carbon- or graphite-containing matrix is a carbon paste.

4. The method according to claim 1, wherein the protein is haemoglobin.

5. The method according to claim 1, wherein the second reagent comprises hydrogen peroxide or a precursor thereof.

6. The method according to claim 5, wherein the second reagent is, or comprises, urea peroxide or sodium perborate.

7. The method according to claim 6, wherein the second reagent is sodium perborate.

8. The method according to claim 1, wherein the first reagent is, or comprises, a compound selected from tetramethylbenzidine, alpha guaiaconic acid, 2,2'-azino bis(3-ethylbenzothiazolidine-6-sulphonic acid), hydroquinone, phenylenediamine, o-dianisidine, o-tolidine (dimethylbenzidine), 6-methoxyquinoline, and 3,3'-diaminobenzidine, 3-amino-9-ethylcarbazole.

9. The method according to claim 8, wherein the first reagent is, or comprises, tetramethylbenzidine.

10. The method according to claim 1, the electrode further holding a wetting additive.

11. The method according to claim 10, wherein the wetting additive is selected from polyvinylpyrrolidone, Triton X, and tween.

12. The method according to claim 10, wherein the wetting additive is present in the electrically conductive matrix at 0.005-0.25 wt %.

13. The method according to claim 1, wherein the electrically conductive matrix is an electrically conductive carbon- or graphite-containing porous matrix.

14. The method according to claim 1, wherein the electrically conductive matrix holds the first reagent.

15. The method according to claim 14, wherein the first reagent is present in the electrically conductive matrix at 1-15 wt %.

16. The method according to claim 1, wherein the electrically conductive matrix holds the second reagent.

17. The method according to claim 16, wherein the second reagent is present in the electrically conductive matrix at 2-15 wt %.

18. The method according to claim 1, wherein the environment to be analysed is a biological sample from a subject.

19. The method according to claim 18, wherein the biological sample is a stool sample.

20. The method according to claim 18, wherein the biological sample is treated with a cell lysing agent.

21. The method according to claim 20, wherein the cell lysing agent is saponin.

22. The method according to claim 18, wherein the subject is on a peroxidase-controlled diet.

23. The method according to claim 1, wherein the pH of the sample is at a pH of 4 to 5.

24. A working electrode for use in the detection of a protein, the working electrode comprising an electrically conductive matrix holding a first reagent and a second reagent, the second reagent being an oxidizing agent or a precursor thereof for the first reagent;
    wherein a reaction between the first reagent and the oxidizing agent is catalysable by the protein to provide a detectable signal at the working electrode; and
    the electrically conductive matrix is an electrically conductive carbon- or graphite-containing matrix or an electrically conductive porous matrix.

25. An electrochemical sensor for use in the detection of a protein, wherein the electrochemical sensor comprises a working electrode comprising an electrically conductive matrix holding a first reagent and a second reagent, the second reagent being an oxidising agent or a precursor thereof for the first reagent;

wherein a reaction between the first reagent and the oxidising agent is catalysable by the protein to provide a detectable signal at the working electrode; and the electrically conductive matrix is an electrically conductive carbon- or graphite-containing matrix or an electrically conductive porous matrix.

26. The electrochemical sensor according to claim 25 further comprising a voltage supply adapted to supply a constant bias between the working electrode and the counter electrode or the reference electrode, where present, a detector for monitoring current, and a controller for controlling the voltage supply and timing of that supply.

27. The electrochemical sensor according to claim 25 further comprising a second working electrode, wherein the second working electrode comprises an electrically conductive matrix holding a first reagent and/or a second reagent, the second reagent being an oxidising agent or a precursor thereof for the first reagent;

wherein a reaction between the first reagent and the oxidising agent is catalysable by the protein to provide a detectable signal at the working electrode; and the electrically conductive matrix is an electrically conductive carbon- or graphite-containing matrix or an electrically conductive porous matrix.

28. The electrochemical sensor according to claim 27, wherein the second working electrode is provided with means for reducing, or preventing in use, exposure of that second working electrode to the protein.

29. The electrochemical sensor according to claim 28, wherein the means is a membrane.

30. The electrochemical sensor according to claim 29, wherein the membrane has pores with an average cross-section of 5 mm or less.

31. A sensing apparatus comprising at least one electrochemical sensor, wherein the apparatus is adapted:
 (i) for use with a sample from a subject;
 (ii) to be swallowable, for passage through the human or animal body;
 (iii) to be implantable in the human or animal body; or
 (iv) to be placed at a surface location of the human or animal body;

and the electrochemical sensor is for use in the detection of a protein, wherein the electrochemical sensor comprises a working electrode comprising an electrically conductive matrix holding a first reagent and a second reagent, the second reagent being an oxidising agent or a precursor thereof for the first reagent;

wherein a reaction between the first reagent and the oxidising agent is catalysable by the protein to provide a detectable signal at the working electrode; and the electrically conductive matrix is an electrically conductive carbon- or graphite-containing matrix or an electrically conductive porous matrix.

32. A kit comprising a sensing apparatus adapted for use with a sample from a subject and further comprising a sampling apparatus for removal of a sample from a stool, wherein the sensing apparatus comprising at least one electrochemical sensor and the electrochemical sensor is for use in the detection of a protein, wherein the electrochemical sensor comprises a working electrode comprising an electrically conductive matrix holding a first reagent and a second reagent, the second reagent being an oxidising agent or a precursor thereof for the first reagent;

wherein a reaction between the first reagent and the oxidising agent is catalysable by the protein to provide a detectable signal at the working electrode; and the electrically conductive matrix is an electrically conductive carbon- or graphite-containing matrix or an electrically conductive porous matrix.

33. A method of preparing a working electrode, the method comprising the step of mixing an electrically conductive matrix with a first reagent and a second reagent thereby to provide a working electrode comprising an electrically conductive matrix holding a first reagent and a second reagent, the second reagent being an oxidising agent or a precursor thereof for the first reagent;

wherein a reaction between the first reagent and the oxidising agent is catalysable by the protein to provide a detectable signal at the working electrode; and the electrically conductive matrix is an electrically conductive carbon- or graphite-containing matrix or an electrically conductive porous matrix.

\* \* \* \* \*